US008774898B2

(12) United States Patent
McGrath et al.

(10) Patent No.: US 8,774,898 B2
(45) Date of Patent: Jul. 8, 2014

(54) OXYGEN-ENHANCED MR IMAGING TECHNIQUE

(75) Inventors: Deirdre McGrath, Manchester (GB); Geoffrey Parker, Manchester (GB)

(73) Assignee: BIOxyDyn Limited, Manchester (GB)

( * ) Notice: Subject to any disclaimer, the term of this patent is extended or adjusted under 35 U.S.C. 154(b) by 44 days.

(21) Appl. No.: 12/988,018

(22) PCT Filed: Apr. 17, 2009

(86) PCT No.: PCT/GB2009/000979
§ 371 (c)(1),
(2), (4) Date: Oct. 15, 2010

(87) PCT Pub. No.: WO2009/127827
PCT Pub. Date: Oct. 22, 2009

(65) Prior Publication Data
US 2011/0035198 A1    Feb. 10, 2011

(30) Foreign Application Priority Data

Apr. 18, 2008 (GB) .................................. 0807144.1
Apr. 3, 2009 (GB) .................................. 0905803.3

(51) Int. Cl.
*A61B 5/00* (2006.01)
(52) U.S. Cl.
USPC ............... 600/410; 600/416; 703/2; 324/309; 382/128
(58) Field of Classification Search
USPC ........... 600/407, 410, 411, 416, 420; 424/9.1, 424/9.3; 436/173; 703/2
See application file for complete search history.

(56) References Cited

U.S. PATENT DOCUMENTS

| | | | |
|---|---|---|---|
| 5,694,934 A | 12/1997 | Edelman | |
| 5,706,805 A * | 1/1998 | Swartz et al. | 600/431 |
| 6,370,415 B1 * | 4/2002 | Weiler et al. | 600/410 |
| 6,589,506 B2 | 7/2003 | Cremillieux et al. | |
| 6,915,151 B2 * | 7/2005 | Baumgardner et al. | 600/420 |
| 7,072,706 B2 | 7/2006 | Baumgardner et al. | |
| 7,867,477 B2 * | 1/2011 | Driehuys et al. | 424/9.3 |
| 2001/0041964 A1 * | 11/2001 | Grass et al. | 702/19 |
| 2002/0043267 A1 * | 4/2002 | Weiler et al. | 128/898 |
| 2004/0129272 A1 * | 7/2004 | Ganesh et al. | 128/207.14 |
| 2005/0022814 A1 * | 2/2005 | Manhard | 128/204.18 |
| 2009/0120435 A1 * | 5/2009 | Slessarev et al. | 128/203.14 |

(Continued)

OTHER PUBLICATIONS

Y Ohno, H Hatabu, D Takenaka, M Van Cauteren, M Fujii, K Sugimara. Dynamic Oxygen-Enhanced MRI Reflects Diffusing Capacity of the Lung. Magnetic Resonance in Medicine 47: 1139-1144 (2002).*

(Continued)

*Primary Examiner* — Unsu Jung
*Assistant Examiner* — Amanda Lauritzen Moher
(74) *Attorney, Agent, or Firm* — Michael Best & Friedrich LLP

(57) ABSTRACT

The present invention relates to a method of characterising tissue function in a subject in need of such characterization. The method comprises performing an imaging technique, on a voxel defined within a tissue space of interest, wherein image data is generated over a time period during which the subject inhales gases with at least two different partial pressures of a paramagnetic gas. A compartmental model algorithm is applied to the image data generated for the voxel to provide information on metabolic function of the tissue.

21 Claims, 11 Drawing Sheets

(56) References Cited

U.S. PATENT DOCUMENTS

Figure 1:
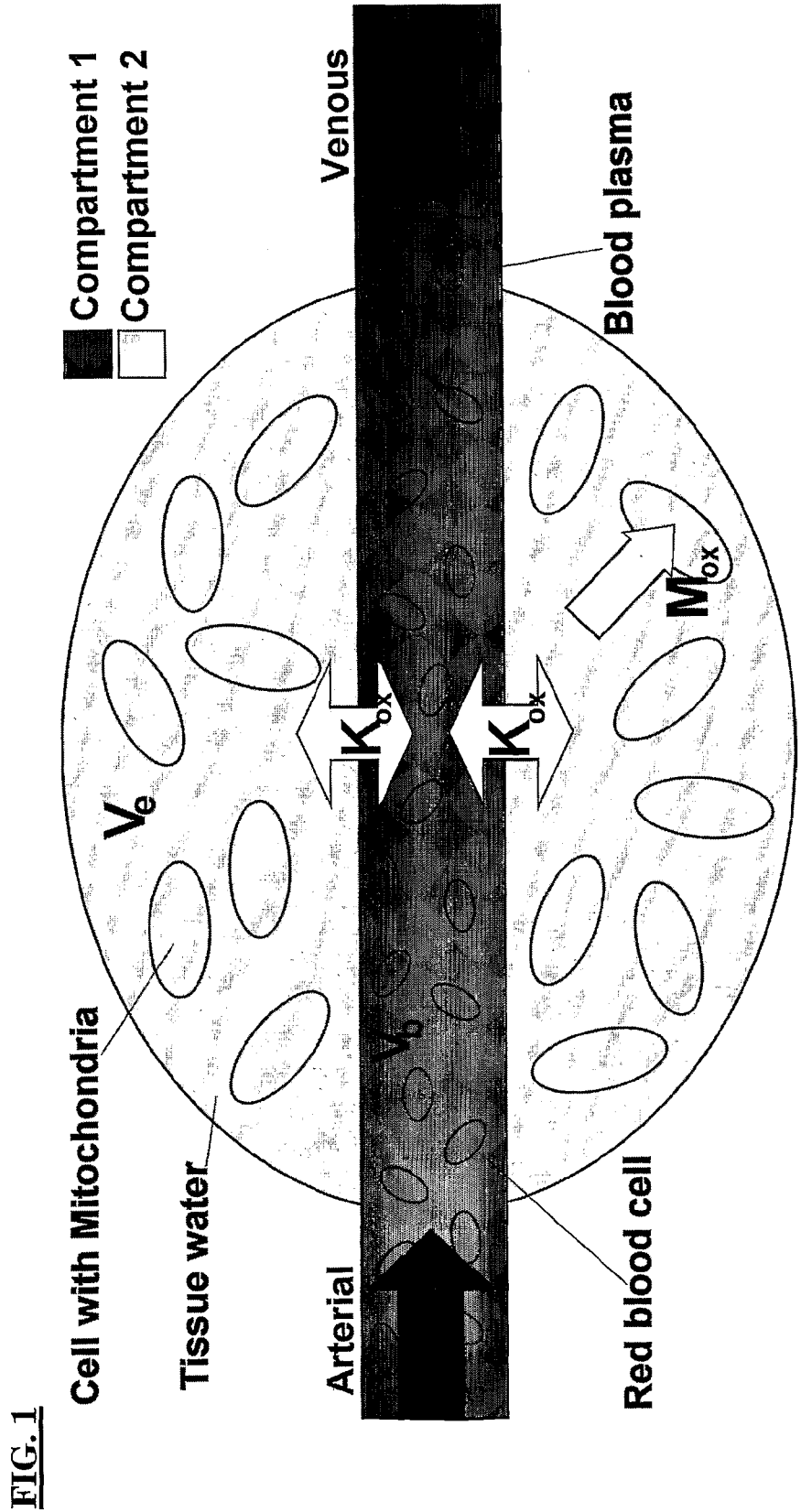

| | | | | |
|---|---|---|---|---|
| 2009/0246138 | A1* | 10/2009 | Santosh et al. | 424/9.2 |
| 2010/0282258 | A1* | 11/2010 | Tailor et al. | 128/204.23 |
| 2011/0104067 | A1* | 5/2011 | Driehuys et al. | 424/9.3 |
| 2012/0215504 | A1* | 8/2012 | Parker et al. | 703/2 |

OTHER PUBLICATIONS

A Stadler, L Stiebellehner, PM Jakob, JFT Arnold, E Eisenhuber, I von Katzler, AA Bankier. Quantitative and Oxygen Enhanced MRI of the Pathologic Lung: Findings in Emphysema, Fibrosis and Cystic Fibrosis. International Journal of Biomedical Imaging (2007).*

C Losert, M Peller, P Schneider, M Reiser. Oxygen-Enhanced MRI of the Brain. Magnetic Resonance in Medicine (2002).*

C Losert, M Peller, P Schneider, M Reiser. Oxygen-Enhanced MRI of the Brain. Magnetic Resonance in Medicine 48:271-277 (2002).*

Rijpkema, M. et al: "Effects of carbogen breathing on tissue oxygenation and perfusion in head and neck tumors as measure by MRI" Proceedings of the International Society for Magnetic Resonance in Medicine, 2001, p. 633, XP0025344470, section 'Patients and Methods', 1 page.

Jarrett F. et al: "The use of hypercapnia in the study of regional cerebral blood flow abnormalities with <133>Xe" Journal of Surgical Research, Academic Press Inc., San Diego, CA, US, vol. 32, No. 2, Feb. 1, 1982, pp. 104-109, XP023022583 ISSN: 0022-4804 [retrieved on Feb. 1, 1982] *p. 104, section 'Introduction', last sentence* p. 104, col. 2, line 13-p. 105, col. 1, line 2, 6 pages.

Fiat D. et al: "In vivo 17O NMR study of rat brain during 17O2 inhalation." Magnetic Resonance in Medicine: Official Journal of the Society of Magnetic Resonance in Medicine/Society of Magnetic Resonance in Medicine Apr. 1992, vol. 24, No. 2, Apr. 1992, pp. 370-374, XP002534471 ISSN: 0740-3194 *section 'Introduction'* second paragraph * p. 371, lines 4-7 * p. 372, equation [1]*, 6 pages.

PCT Search Report and Written Opinion for PCT/GB2009/000979, dated Jul. 9, 2009, 15 pages.

XP002488377, Database Medline [Online]. US National Library of Medicine (NLM). Bethesda, MD, US: Jun. 2002, Ohio Yoshiharu et al: "Dynamic oxygen-enhanced MRI reflects diffusing capacity of the lung." Database accession No. NLM12111960, p. 1140, left-hand column and p. 1143, left-hand column & Magnetic Resonance in Medicine: Official Journal of the Society of Magnetic Resonance in Medicine / Society of Magnetic Resonance in Medicine Jun. 2002, vol. 47, No. 6, Jun. 2002, pp. 1139-1144, ISSN: 0740-3194.

XP002488378, Database Medline [Online], US National Library of Medicine (NLM), Bethesda, MD, US; Aug. 2005, Naish Josephine H et al: "Improved quantitative dynamic regional oxygen-enhanced pulmonary imaging using image registration." Database accession No. NLM 16032679 cited in the application p. 465 paragraph 3 & Magnetic Resonance in Medicine: Official Journal of the Society of Magnetic Resonance in Medicine / Society of Magnetic Resonance in Medicine Aug. 2005, vol. 54, No. 2, Aug. 2005, pp. 464-469, ISSN: 0740-3194.

XP002488379, Database Medline [Online], US National Library of Medicine (NLM), Bethesda, MD, US; May 2004, Jakob Peter M. et al: "Assessment of human pulmonary function using oxygen-enhanced T(1) imaging in patients with cystic fibrosis." Database accession No. NLM15122684 cited in the application abstract & Magnetic Resonance in Medicine: Official Journal of the Society of Magnetic Resonance in Medicine / Society of Magnetic Resonance in Medicine, May 2004, vol. 51, No. 5, May 2004, pp. 1009-1016, ISSN: 0740-3194.

XP002380246, Tofts P S et al: "Estimating Kinetic Parameters From Dynamic Contrast-Enhanced T1-Weighted MRI of a Diffusable Tracer: Standardized Quantities and Symbols" Journal of Magnetic Resonance Imaging, Society for Magnetic Resonance Imaging, Oak Brook, IL, US, vol. 10, No. 3, Sep. 1, 1999, pp. 223-232, ISSN: 1053-1807.

XP009103075, Seymour S. Kety: "The Theory and Applications of the Exchange of Inert Gas at the Lungs and Tissues" Pharmacological Reviews, Williams and Wilkins Inc., Baltimore, MD, US. vol. 3, Jan. 1, 1951, pp. 1-41, ISSN: 0031-6997.

XP009103081, Johnson and Wilson, "A model for capillary exchange" American Journal of Physiology, American Physiological Society, Bethesda, MD, US, vol. 210, Jan. 1, 1966, pp. 1299-1303, ISSN: 0002-9513.

\* cited by examiner

FIG. 5

| Pt | Age | Tumour histology | Stage | Tumour site | Lesion | Previous therapy | Mean $\Delta R_1$ air to $O_2$ ($s^{-1}$) | 95% CI ($s^{-1}$) | p value |
|---|---|---|---|---|---|---|---|---|---|
| 1 | 56 | Clear cell ovarian carcinoma | IV | Liver | 1 | Cytotoxic CT | 0.0526 | 0.0406 – 0.0646 | <0.001 |
| 1 | 56 | Clear cell ovarian carcinoma | IV | Liver | 2 | Cytotoxic CT | 0.0259 | 0.0180 – 0.0337 | 0.006 |
| 2 | 80 | Ovarian carcinosarcoma | IIc | Omentum | 1 | Cytotoxic CT | 0.0463 | 0.0240 – 0.0686 | 0.004 |
| 3 | 73 | Gastric adenocarcinoma | Metastatic | Liver | 1 | None | 0.0214 | 0.0038 – 0.0389 | 0.198 |
| 3 | 73 | Gastric adenocarcinoma | Metastatic | Liver | 2 | None | 0.0318 | 0.0138 – 0.0499 | 0.064 |
| 4 | 51 | Endometrioid ovarian cancer | II | Pelvis | 1 | RT/ Cytotoxic CT | 0.0459 | 0.0404 – 0.0514 | <0.001 |
| 5 | 52 | Ovarian serous adenocarcinoma | IIIb | Pelvis | 1 | Cytotoxic CT | 0.0087 | 0.0032 – 0.0142 | 0.003 |

OXYGEN-ENHANCED MR IMAGING TECHNIQUE

CROSS-REFERENCE TO RELATED APPLICATIONS

This patent application is a national stage filing under 35 U.S.C. 371 of International Application No. PCT/GB2009/000979, filed 17 Apr. 2009, which claims foreign priority to Great Britain Patent Application No. 0905803.3, filed 3 Apr. 2009 and 0807144.1, filed 18 Apr. 2008, each of which is incorporated herein in its entirety. Priority is hereby claimed to each of these applications.

The present invention relates to methods for imaging tissues and in particular to the application of a compartmental model to (but not limited to) oxygen-Enhanced Magnetic Resonance Imaging (OE-MRI).

Nuclear magnetic resonance (NMR) involves applying a magnetic field that acts on the nuclei of atoms with fractional spin quantum numbers and thereby polarizes them. During measurements, radio-frequency pulses of given resonance energy are applied that flip the nuclear spins and disturb the orientation distribution. The nuclei then return (relax) to the initial state in a time dependent exponential fashion and thereby give a signal that may be electronically processed into recordable data. When the signals are spatially differentiated and of sufficient level, the data can be organized and displayed as images on a screen. For instance, computing the signals generated by the protons of water within organic tissues makes it possible to construct magnetic resonance images (MRI) allowing direct visualization of internal organs in living beings. NMR is therefore a powerful tool in diagnostics, medical treatment and surgery.

It will be appreciated that a clinician will wish to test the metabolic function of tissues within in a subject for a number of reasons. In the initial stages of diagnosis of a patient when little or nothing is known about the health of the subject, metabolic function tests can give an indication of the general health of a patient. Moreover, in many illnesses lesions can occur in tissue areas of a subject. Such tissue areas may become the focus of interest for a clinician for the purposes of diagnosis, treatment, surgery planning or prognostic assessment. Characterising the metabolic function of such a tissue area of interest can help to diagnose illness, guide treatment or surgery, or to help the clinician to give a prognosis for the progression of illness. For example, tissue which has been damaged in some way may exhibit altered metabolic function, or indeed no metabolic function at all. In particular, tumorous tissue can exhibit increased or reduced metabolic function. A clinician may, for example, use altered metabolic function to identify or characterise tumours in a subject. In some cases, increased metabolic function may be used to give prognoses regarding likely areas of new growth of the tumour.

Positron Emission Tomography (PET) is a nuclear medicine technology which is capable of producing low resolution images which may be used to characterise the function of tissue in a subject. During a PET scan, a radioisotope is introduced into the subject and a scanner detects the scintillations of the radioisotope. In this way, the radioisotope is located within the subject and its passage through the subject can be tracked. $^{15}O$ is a commonly used contrast medium in PET imaging. Unfortunately, the technology is limited by the resolution of the images which are produced and by the necessity of using radio-isotopes.

Dynamic contrast-enhanced MRI (DCE-MRI) has also been used to characterise tissue function in the past. An inert exogenous contrast medium, which is visible in images produced by an MRI scan, is introduced into the blood supply of a subject and the subject is scanned. The resulting images, which show the perfusion of the contrast medium through the subject, may be used to characterise elements of tissue function such as blood perfusion through the tissues and also the permeability of the tissues to the contrast medium. However these methods do not provide direct information on oxygen delivery or metabolism in tissues. An alternative identified but uncommon contrast medium used in MRI is $^{17}O$, which is expensive and difficult to acquire.

The abovementioned imaging techniques are capable of characterising tissue function in a subject. However, their use is limited by the fact that they require the use of (often nuclear medicine-based) contrast media. The introduction of a "foreign" contrast medium into a subject can have serious pathophysiological consequences. For instance there are well documented risks of introducing radioactive contrast media into a subject. For these reasons, it is commonly the case that the most vulnerable patients are not suitable for these imaging techniques.

OE-MRI has previously been demonstrated as an indirect method to visualize lung ventilation. Molecular oxygen ($O_2$ of any isotope and importantly $^{16}O$, which is non-radioactive) is paramagnetic and so acts as an NMR contrast agent when dissolved in parenchymal water due to its effect on $T_1$ ($T_1$ is known to those skilled in the art of NMR as the named spin-lattice relaxation time and is the time constant in the z-direction, which is taken to be parallel with the applied magnetic field). Breathing 100% oxygen results in an increase in the concentration of dissolved oxygen in the lung tissue producing a corresponding decrease in $T_1$ which can be detected as a regional signal intensity increase in a $T_1$-weighted image. Studies have been performed which analysed the time taken to reach saturation of oxygen in the lung tissues when breathing 100% oxygen, and the time taken for the concentration of oxygen in the lung tissues to return to normal after breathing of the 100% oxygen has ended. These are known as wash-in and wash-out times.

OE-MRI has also been used to analyse tissue function in a number of areas in the body: in the renal cortex, spleen, liver, muscle and in tumours.

OE-MRI provides many advantages over DCE-MRI, $^{17}O$ for MRI and $^{15}O$ for PET imaging in that atmospheric oxygen, or $^{16}O$, is abundantly available and safe to use. $^{16}O$ is non-ionising, as opposed to $^{15}O$, which makes $^{16}O$ safer to use. $^{16}O$ is also cheaper and easier to acquire than either of $^{17}O$ or $^{15}O$.

It is therefore an object of the present invention to overcome problems associated with prior art scanning methods (e.g. PET, DCE-MRI and OE-MRI methods) and provide a technique that will provide clinically significant information about tissue function and physiology in both healthy and diseased states.

According to a first aspect of the present invention there is provided a method of characterising tissue function in a subject in need of such characterisation comprising:
  performing an imaging technique, on a voxel defined within the subject,
  wherein image data is generated over a time period during which the subject inhales gases with at least two different partial pressures of a paramagnetic gas,
  and applying a compartmental model algorithm to the image data generated for the voxel to provide information on metabolic function of tissue within the voxel.

The imaging technique may be any appropriate imaging technique known to the skilled person. For instance it may be any form of MRI, CT scanning, X-ray etc. However it is preferred that the imaging technique is MRI.

The paramagnetic gas may be any appropriate paramagnetic gas although it is preferred that the paramagnetic gas is oxygen.

When the imaging technique is MRI it is preferred that the paramagnetic gas is oxygen. Alternatively, when MRI is used, the paramagnetic gas may be an aerosol or other contrast media such as gadolinium-based aerosols that cause a signal change in tissues when observed with MRI.

It is most preferred that the imaging technique is oxygen-Enhanced Magnetic Resonance Imaging (OE-MRI).

It is preferred that the image data provides information in respect of delivery of oxygen to a tissue and metabolic consumption of oxygen within tissue.

The method of the first aspect of the invention allows normal and abnormal tissue function to be evaluated and provides important data that is useful for making a diagnosis and also giving a prognosis for subjects with disease (e.g. subjects with a lesion such as a tumour or other incorrectly functioning area of tissue) or those who are predisposed to such damage or disease (e.g. from environmental causes or for genetic reasons).

By the term "voxel" we mean a volume element in a grid defined by a 3-dimensional space within the subject. In the present invention, it is preferred that the subject is divided into a matrix of voxels that are each typically a few cubic millimeters.

The present invention is based upon the inventors knowledge in the field of MRI, and particularly OE-MRI, and image processing. They have appreciated that OE-MRI is useful for visualising oxygen delivery and metabolic function in tissues because when in an aqueous environment (e.g. in the interstitial fluid, inside cells or in plasma) oxygen will interact with protons in water and therefore result in an altered NMR signal. The present invention was made when the inventors were considering whether or not these MRI properties of oxygen would make it possible to obtain meaningful data relating to tissue function from OE-MRI. They realised that the difference in concentration between oxygen in tissues and in blood may allow them to use OE-MRI to measure the rates at which oxygen was delivered to tissues and consumed by metabolic processes within the tissues of interest. Such data would be of great value because they would provide a clinician with informative data regarding the health status of the tissues of interest. A clinician will appreciate that there are numerous situations (e.g. tumorous illnesses such as cancer) where the levels of oxygen, the rate of metabolisation in particular, and cellular respiratory function in general, are good indicators of health of healthy tissue and are also good indicators of likely areas of new growth in tumorous tissue, and that a technique for visualising areas of tissue suffering either enhancement or impairment of function would be very powerful for making a diagnosis or prognostic assessment.

The inventors further realised that OE-MRI could be a powerful technique because the voxel size could be set quite small and NMR used to visualise the whole of a tissue or tumour and a surrounding area by detecting an NMR signal from a matrix of voxels that extend throughout the whole of the tissue or tumour and the surrounding area or a proportion thereof. Accordingly the method of the invention preferably involves conducting OE-MRI on "n" voxels forming a matrix within the tissue of interest. The efficiency of gaseous exchange can be measured for each voxel and a clinician may then be presented with specific information on perfusion, oxygen diffusion and oxygen metabolisation in discrete areas of a tissue area of interest.

The inventors appreciated that the best way of calculating the rate of oxygen consumption in a tissue of interest would be to analyse the transfer of oxygen from the arterial and venous spaces (a first compartment) into the tissues (a second compartment) by continuous dynamic acquisition of NMR data from the tissues while the gas supply was switched between gas mixtures of varying partial pressures of oxygen, resulting in a variation in the concentration of gaseous oxygen arriving at the tissues. In principle, this may be achieved by requiring a subject to breathe in at least two different concentrations of oxygen. The MRI data collected when the subject is breathing the different concentrations of oxygen can be used to calculate the rate of metabolic oxygen consumption using the algorithm discussed in more detail below.

A further important factor that contributed to the realisation of the invention is that the inventors appreciated that the oxygen that is diffused into the tissues is consumed by the metabolic processes at work in the tissues. Furthermore the inventors realised that the metabolic consumption of oxygen can be a very important factor when making a pathophysiological assessment of a subject and as such they endeavoured to develop a method that would be particularly useful for assessing metabolic consumption of oxygen in tissues. Accordingly one important feature of the method of the invention is that this effect can be factored into the algorithm used according to the invention.

The measurement of metabolic consumption of oxygen is not possible using many other methods of medical imaging, including gadolinium-based DCE-MRI, because these imaging modalities do not measure oxygen content. The inventors have realised that, although the metabolic consumption of oxygen cannot be directly measured from imaging data relating to oxygen, such as OE-MRI data, a measurement may be inferred from MR signals generated as a result of oxygen in surrounding matter within a subject over time. Thus, the inclusion of a metabolic factor in the algorithm of the invention is significantly advantageous over any prior art method of imaging tissue function since, without such a factor, no measurement of metabolic function could be obtained from the MRI data.

Subjects tested according to the method of the invention may be any subject for whom it is desirable to test the cellular respiratory function or metabolic function of tissues. The subject is preferably a mammal (although the methodology is also generally applicable to any organism, such as birds, reptiles, amphibians) and the method is particularly suitable for testing tissue function in animals of veterinary importance (e.g. horses, cattle, dogs or cats), or animals important in therapeutic (including but not limited to pharmacological) development work (e.g. mice or rats). However it will be appreciated that the subject is preferably a human.

The method is particularly useful for investigating whether or not human subjects have conditions that are characterised by changes in cellular respiratory function (i.e. changes in the metabolism of oxygen). Alternatively tissues in a subject may be imaged to evaluate how such a condition is progressing over time (e.g. in response to medical or surgical intervention). Such conditions include cancers/tumours that often consume oxygen at a different rate to "normal" tissue. Infections (e.g. meningitis), inflammatory conditions (e.g. Crohn's disease), fibrotic conditions (e.g. pulmonary fibrosis) and immunological conditions (e.g. autoimmune disease) may all cause tissues to exhibit altered metabolic activity and can therefore be imaged according to the methods of the invention. It is preferred that the methods are used to image tumours.

It will also be appreciated that the methods of the invention can be utilised to test how a subject responds to a candidate drug wherein the drug is being assessed to evaluate if it has an influence (directly or indirectly) on the oxygen levels in a tissue of interest. This may be in a clinical trial of human subjects or may even be as part of a research programme for testing candidate drugs in animal subjects.

In particular the methods can be employed to evaluate whether or not a candidate drug is able to modulate the metabolic activity of a tissue at which it acts. For instance candidate drugs for use in the treatment of cancer may be assessed by evaluating the metabolic activity (i.e. oxygen consumption) of a tumour before a drug is applied (which may be greater than for untransformed cells) and then comparing this with the metabolic activity of the tumour after the subject has been treated with the candidate drug (a useful candidate may be expected to reduce the metabolic activity of the tumour). Such screens may preferably be used to assess the usefulness of candidate drugs for treating solid tumours (for instance tumours of the liver, bladder, stomach, colon or lung).

Alternatively screens may be performed for drugs that are candidate anti-inflammatory agents (inflamed tissues may be expected to exhibit high oxygen consumption whereas an efficacious anti-inflammatory agent may be expected to reduce oxygen consumption in an inflamed tissue).

A skilled person will be appreciated that the method will be useful as a screen for a number of pathophysiological conditions that are known to be characterised by increased or decreased oxygen consumption when compared with normal healthy tissues.

Subjects to be tested should be placed in an MRI machine typically but not necessarily at 1.5 tesla magnetic field strength. As the method requires little specialist equipment it should be possible to use OE-MRI in any MRI machine designed for human or animal use.

The subject inhaling gases with at least two different partial pressures of a paramagnetic gas may be fitted with a mask or breathing apparatus for gas delivery in order that different gases may be inhaled while the MRI scans are performed. When the gas is oxygen room air may be used as one of the partial pressures of oxygen in which instance the subject would breathe normally without the use of any apparatus.

It is preferred that the subject inhales two gases—a first gas has a relatively low concentration of oxygen (e.g. 10%-35%) and the other gas contains a relatively high concentration of oxygen (e.g. 45%-100%). It is most preferred that the first gas is air (comprising approximately 21% oxygen) and the other is a gas comprising an oxygen content of 90%-100%. It will be appreciated that the choice of gases used may depend on the health status of the subject.

Before the beginning of a scan using dissolved oxygen as a contrast agent, the concentration of dissolved oxygen within the tissues of a live subject is always greater than zero because the subject has been continuously breathing air, from which oxygen has been extracted and perfused to the tissues in the subject's blood. This is different to imaging techniques in which artificial contrast agents, such as $^{17}O$ or $^{15}O$, are used because these are not naturally occurring substances in significant abundance, therefore their concentration in the tissues of a subject before a scan can be assumed to be zero. Providing a first gas, of a first concentration of oxygen, allows baseline signals to be detected for dissolved oxygen concentration within the tissues in the area of interest. Providing another gas, of a different concentration, during scanning allows the changes in dissolved oxygen concentration within the tissues to be detected during a transition period in which the concentration of oxygen within the tissues increases due to the increase in the concentration of oxygen which is breathed by the subject. Further measurements may then be made during breathing of this gas.

The subject may revert back to breathing the first gas or to another concentration of gas. In this event, measurements are preferably made which detect the change in concentration of dissolved oxygen within the tissues during this further transition period. Transitions between each gas may be repeated as needed. This method provides a more accurate measurement of local concentrations of oxygen within the tissues, and rates of metabolic consumption of oxygen, than can be obtained simply by measuring oxygen concentrations for a single gas. The time taken for a transition from a lower to a higher concentration of oxygen is known as the "wash in" time. The time taken for a transition from a higher to a lower concentration of oxygen is known as the "wash out" time. The length of wash in time and wash out time are approximately equal for a single subject during a single scanning period and, accordingly, the approximate length in seconds of the wash in and wash out times for a single subject during a single scanning period is indicated herein by a single value.

The total partial pressure (or concentration) of MRI visible oxygen (in units of mmHg) in any given voxel of the subject is defined herein as $PO_2$. The concentration of oxygen in the blood alone is defined herein as $P_aO_2$. The concentration of oxygen in the other tissues (i.e. non-blood) is defined herein as $P_eO_2$. Accordingly $PO_2 = P_aO_2 + P_eO_2$. It will be appreciated that in some instances $PO_2$ may be referred to when it is clear in the context of the disclosure that reference is being made to the partial pressure of oxygen in a particular tissue. For Example a reference to $PO_2$ of blood is clearly the same as reference to $P_aO_2$.

It will be appreciated that blood vessels carry inhaled oxygen from the lungs to tissues of interest. It is therefore preferred that the compartmental model algorithm according to the invention takes account of the wash in and wash out times for the blood (which includes the time taken for arterial oxygen concentrations to reach a maximum or return to baseline, which is a function of the efficiency of ventilation and other lung health factors). The wash in and wash out time for the blood is indicated herein by the value ($T_{OIF}$). $T_{OIF}$ can be estimated from known physiological averages and taken to be a single uniform value across the entire vascular system of a subject. As described below, $T_{OIF}$ can be useful according to the invention because it can be used to calculate the partial pressure of oxygen in the blood ($P_aO_2$), which is then used as an input to the compartmental model algorithm. Alternatively a measurement of the oxygen concentration in the blood ($P_aO_2$) may be performed either using OE-MRI methods focusing on voxels that only comprise blood (e.g. see the method of example 4) or alternative methods such as via blood sampling, and these measurements can be used to produce more accurate values representing $P_aO_2$ across the entire vasculature of the subject. In some embodiments, the value of $P_aO_2$ is measured using OE-MRI data taken from the region of the aorta.

It is preferred that OE-MRI data is recorded for each voxel by starting a subject on a low concentration of oxygen; swapping the inhaled gas to one with a high oxygen concentration for a period of time; and then returning the subject to inhaling the low oxygen concentration gas again. The method of the invention most preferably generates OE-MRI data from a subject wherein 100% oxygen is washed-in and washed-out when individuals are breathing normal air (e.g. medical air comprising 21% oxygen) before and after the 100% oxygen is inhaled. The differing concentrations of the oxygen, acting as a contrast medium, then influence the NMR signal detected from protons (primarily from water or lipids in the tissue but potentially from other proton-carrying molecules that are visible using NMR, such as N-acetyl aspartate, creatine, lactate or choline) or from molecules containing other NMR-sensitive nuclei (such as $^{31}P$, $^{19}F$, $^{23}Na$, $^{17}O$) and this OE-MRI data may then be used to create the input for the algorithm used according to the invention. The compartmental model algorithm according to the invention may be fitted to the OE-MRI data. Most preferred regimens are described in the examples.

The OE-MRI data may be the $T_1$ spin-lattice relaxation time $R_1$ (which is directly derived from the $T_1$ signal as $R_1 = T_1^{-1}$) in units of $s^{-1}$. In order to convert the $R_1$ value to a value which is indicative of $PO_2$, it is necessary to use a conversion factor. While it is appreciated that any desirable conversion factor may be used, a preferred conversion factor is $r_1 = 4 \times 10^{-4} s^{-1} mmHg^{-1}$, which is an accepted factor that has been established empirically. An alternative conversion factor is $2.49 \times 10^{-4}$, which was validated by Zaharchuk G, Busse R F, et al. (Acad Radiol 2006; 13:1016-1024). $R_1$ (in $s^{-1}$) may be converted to $PO_2$ (in mmHg) by dividing $R_1$ by $r_1$ (in $s^{-1}$ $mmHg^{-1}$). Given that the conversion factor is applied as a linear factor to the entire MRI dataset of $R_1$ values, it will be appreciated that a specific value of the conversion factor is not critical when the methods are used to assess differences in oxygen level and particularly metabolic consumption. The factor is used to convert the MRI data values into the range of oxygen partial pressures (or concentrations).

In individuals with healthy lung function and healthy vasculature the Oxygen-Enhanced MRI signal of tissues of interest will have increased and reached saturation within approximately 5 min. The time for the signal to decrease to its normal baseline value when the gases are switched back to air is also within the same time frame of approximately 5 min. However, these time scales may vary from organ to organ and in disease. Typically the subject will be required to breathe a gas mixture or mixtures with a higher concentration of oxygen for a maximum period of approximately 10 minutes. Adverse effects from breathing higher concentrations of oxygen have only been noted after approximately 24 hours exposure, and therefore this length of exposure is deemed safe and without any detrimental effects for the majority of subjects.

A challenge in using MRI to image a live subject is the problem caused by movement of the subject during scanning. For instance a subject's rib cage will move while breathing and a subject may make a number or involuntary, or even be unable to prevent voluntary, movements from occurring. This causes a technical challenge when an MRI signal needs to be measured from a single voxel over time. It is therefore preferred that image registration techniques are applied to ensure that measurements can be made from the same volume of tissue. An example of a preferred image registration technique is that may be used according to the method of the invention was developed by Naish et al. (Naish et al. (2005) Magnetic Resonance in Medicine 54:464-469).

The invention has been based on the realisation that a compartmental modelling approach may be applied to OE-MRI to allow the extraction of parameters from the enhancement information that give more specific information on local metabolic function in tissues. The compartmental model may be based on a first compartment which is the vascular space (containing oxygen at a partial pressure of approximately 95 mmHg in the arteries and 40 mmHg in the veins during air breathing) and a second compartment including the tissue cells and interstitium (containing oxygen dissolved in tissue water with an oxygen partial pressures of approximately 40 mmHg during air breathing).

It will be appreciated that the development of such a model represented considerable technical hurdles. The inventors therefore applied considerable inventive endeavour to develop a compartmental model for OE-MRI of bodily tissues that allows the calculation of parameters describing metabolisation of oxygen in the tissues.

One particular realisation of the inventors has been that OE-MRI data may be used in such a way as to generate information relating to aspects of tissue function which other contrast enhanced methods, such as MRI using $^{17}O$ and PET using $^{15}O$ may not be able to measure. By analysing the data generated by OE-MRI of a tissue space of interest, information may be generated which relates directly to the metabolisation of oxygen in the tissue space. This information is not directly measurable using OE-MRI but the inventors have realised that it may be inferred from direct measurements over time using compartmental modelling.

The method according to the invention is preferably a two-compartment model based on known physiological parameters for concentration of oxygen in blood and tissue. Such a compartmental model preferably models the combined oxygen concentration of a voxel ($C_T$) as consisting of a first compartment ($C_b$), comprising blood which is present in the blood vessels, in particular the arteries, arterioles and capillaries, of the subject; and a second compartment ($C_e$), comprising tissue cells and the interstitial space between the cells obtained from the changing NMR signal values.

It will be appreciated that measured values, for example of dissolved oxygen concentration, may be input to the compartmental modelling algorithm used according to the invention and/or the compartmental model according to the invention may be fitted to the measured values. Accordingly the value $PO_2$, derived from $R_1$ as described above, may be used as input to the model that is equivalent to $C_T$. In this respect, the model parameter $C_T$ represents the total oxygen concentration in a voxel over the period of a scan, the model being fitted to the measured values of dissolved oxygen concentration for each voxel (i.e. the $PO_2$ values derived from $\Delta R_1$). Furthermore, it will be appreciated that $C_b$ may be inferred or measured ($C_b$ may be equal to $P_aO_2$, which may be inferred or measured) and used as an input to the algorithm.

In some embodiments, $C_b$ may not be inferred or measured, and is not therefore an input to the model. Rather, $C_b$ can be modelled in the compartmental model by introducing parameters which define the shape of $C_b$ into the model. The basic shape of $C_b$ is known to follow a trapezoidal_function. One or more parameters of this trapezoidal function (such as $T_{OIF}$ which determines the gradient of the trapezoidal function during washing in and washing out of the increased concentration of oxygen) can be used as parameters to the model. In such a formulation of the model, Cb and its parameters, such as $T_{OIF}$, may be outputs from the model and represent scientifically and clinically useful information.

It is also preferred that the compartmental model takes into account one or more of the following parameters, or facilitates the calculation of such parameters: the fractional volume of blood per MRI visible matter ($V_b$); the fractional volume of tissue per MRI visible matter ($V_e$); diffusing capacity of the vasculature ($K_{ox}$); the rate of metabolic consumption of oxygen within the second compartment ($M_{ox}$); and also the parameters describing the shape of the input function which defines the predicted oxygen concentration in blood arriving at the tissue area of interest (i.e. the time-lag between inhalation of an elevated level of oxygen and the maximum input oxygen concentration within the tissues, or wash-in time $T_{OIF}$).

In one of the preferred embodiments in which $K_{ox}$ is measured, it will be appreciated that $K_{ox}$ is entirely different to the value $k^{trans}$ which is output by DCE-MRI techniques. $k^{trans}$ is a measure of the diffusion of a contrast medium (such as a gadolinium-based contrast medium) from blood into tissue. Contrast media provide a contrast to what is already there, and as such are foreign to the subject and would not naturally be diffused into the tissues (or, at least, not in as large quantities as is the case during DCE-MRI). Thus, the $k^{trans}$ measurement is of the "leakiness" of a particular area of vasculature to foreign media. In contrast, $K_{ox}$ is a measure of the diffusion of oxygen from blood into tissue, which is a natural process. Accordingly, $K_{ox}$ is useful in measuring how well oxygen travels to tissue from blood, a purpose for which $k^{trans}$ is wholly inappropriate.

It is particularly preferred that the compartmental model takes into account the amount of oxygen in the blood, the amount of diffused oxygen in the tissues, and the rate at which oxygen is dissolved into the tissues from the blood.

It is most preferred that the compartmental model takes into account, and can provide output data relating to, the rate at which the dissolved oxygen is removed from tissue by metabolic consumption ($M_{ox}$). This realisation that a model can provide information about the rate of metabolisation of oxygen is considered a particular advantage of the method of the invention.

The model used according to the invention may be based on other numbers (i.e. greater than two) of model compartments, such as a three compartment model which again assigns the arteries as the first compartment, the tissue and interstitium as the second compartment and the veins as the third compartment.

It will generally be appreciated that the particular formulation of the compartmental model described here is not to be interpreted as a limitation of the applicability of the algorithm according to the invention. In general, any parameter of interest, such as $M_{ox}$ or $K_{ox}$, which contributes to (or otherwise affects) the total concentration of oxygen in a given voxel may readily be inserted into the model. Values may then be obtained for that parameter by fitting the model to medical imaging data relating to the oxygen concentration for that voxel.

It is preferred that the compartmental model is an adaptation of the equations developed by Kety (Kety, S S (1951) Pharmacological Reviews. 3: 1-41) which described the rate of diffusion of gases across the alveolus membrane to pulmonary capillary blood. The realisation that this model for gas transfer can be modified so as to be usable in order to model oxygen metabolisation in tissues is a major technical problem which has been overcome by the inventors.

Therefore the method of the first aspect of the invention preferably applies a compartmental model algorithm based on the Kety two compartment model. The algorithm is applied to OE-MRI data obtained by washing-in and washing-out inhaled gases with at least two different partial pressures of oxygen. Preferably MRI measurements will be made on a tissue area of interest within a subject who starts breathing normal air (21% oxygen); 100% oxygen is then washed-in and maintained for defined time period (e.g. 5 minutes); and the 100% oxygen is then washed-out by returning to breathing normal air (21% oxygen). The differing concentrations of the oxygen, acting as a contrast medium, then influence the NMR signal detected from protons and this OE-MRI data is then used as a function to be fitted by a two-compartment model according to the invention.

It will be appreciated that a number of different algorithms may be developed for use according to the method of the first aspect of the invention. It will be further appreciated that one reason for an inventive step of the method of the invention is that the inventors were the first to appreciate that a compartmental model, and in particular a modification of the Kety model, could be applied to OE-MRI data from tissues which are not tissues within the lung (despite the problems encountered with such techniques).

In a preferred embodiment of the invention, the inventors developed an algorithm by applying the following proof:

The first compartment is the blood and the oxygen concentration in the first compartment may be denoted by $C_b$ (corresponding to $P_aO_2$) and the second compartment includes the tissues and the interstitial space between the tissues, with a combined oxygen concentration denoted by $C_e$ (corresponding to $P_eO_2$) (see FIG. 1). The fractional volume of a voxel which is blood is denoted by $V_b$ and the fractional volume of the voxel which is tissue or interstitium is denoted by $V_e$. The measured concentration of oxygen $C_T$ (corresponding to $PO_2$) may therefore be derived from equation (I):

$$C_T = V_b C_b + V_e C_e, \tag{I}$$

The inventors then developed a model by assuming that $V_b = 1 - V_e$. Equation (I) could therefore be approximated as set out in equation (II):

$$C_T = (1 - V_e) C_b + V_e C_e \tag{II}$$

Kety introduced a two-compartment model relating to modeling of inert gas transfer. The inventors have realized that a two compartment model can be used to model tissue function from OE-MRI data by adapting the Kety model.

Accordingly the inventors have adapted the Kety model such that the observed rate of change in oxygen concentration in the extra vascular compartment, $C_e$, during the administration of elevated oxygen concentrations (i.e. >21% of room air), can be modelled using an expression incorporating a term for the rate of transfer of oxygen across the capillary boundaries ($K_{ox}$). An additional term is used to define the rate at which oxygen is absorbed or metabolized within the tissues ($M_{ox}$), hence equation (III):

$$V_e \frac{dC_e}{dt} = K_{ox}(C_b - C_e) - M_{ox} C_e \tag{III}$$

The additional term for $M_{ox}$ is not present in either Kety's model or any subsequent DCE-MRI based compartmental model. The term has been added here after a realisation by the inventors that a term $M_{ox}$ would be indicative of the rate of metabolic consumption of oxygen within a voxel of interest. This term therefore represents a diagnostic or prognostic measure, which is borne out by the results in example 2. The term $M_{ox}$ may be assumed to represent a metabolic consumption of oxygen that depends linearly on the concentration of oxygen in the tissue. Alternative formulations may impose other forms on this relationship, such as the definition of a maximum concentration beyond which the metabolic consumption of the tissue is unchanged. It will generally be appreciated that any aspect of tissue function which contributes to (or otherwise affects) the total concentration of oxygen in a given voxel may readily be inserted into equation (III) in the same way as $M_{ox}$ or $K_{ox}$ in this exemplary model.

Based on these calculations the inventors realised that it would be possible to solve $C_e$ (i.e. $P_eO_2$, the combined oxygen concentration of the second compartment comprising the tissues and interstitium, calculated as described above) using equation (IV):

$$C_e = \frac{K_{ox}}{V_e} \int C_b(\tau) \exp\left(-\frac{K_{ox} + M_{ox}}{V_e}(t-\tau)\right) d\tau. \quad \text{(IV)}$$

The identity of equation (IV) was then used by the inventors to develop an equation which relates to the measured concentration of oxygen $C_T$ (i.e. $PO_2$) in any given voxel by substituting equation (IV) into equation (II), as set out in equation (V):

$$C_T = (1-V_e)C_b + K_{ox} \int C_b(\tau) \exp\left(-\frac{K_{ox} + M_{ox}}{V_e}(t-\tau)\right) d\tau. \quad \text{(V)}$$

Clinically meaningful information may be attached to values for $M_{ox}$, $K_{ox}$ and $V_e$. The model allows the calculation of these parameters using any appropriate algorithm (such as the Levenberg Marquardt non-linear least squares fitting algorithm) which allows the fitting of the functional form described by the compartmental model $C_T$ (see equation (V) above) to the dynamic oxygen concentration dataset calculated from the changing NMR signals in the tissue area of interest.

The data generated by applying the fitting algorithm can then be displayed as an image (in two or three dimensions) of the subject wherein the tone of each pixel of the image are representative of one of the parameters output by the model for a corresponding voxel.

The method of the present invention is particularly useful for both prognostic and diagnostic purposes in relation to tissue function, particularly in the case of tissue lesions such as tumours. However, in a preferred embodiment the method will be of particular use in prognostics and in the development and monitoring of drug therapies. Prognostic use could also include the identification of patients who are more or less likely to respond to a given treatment option, which could enhance patient selection criteria for therapy.

This technique of measuring regional tissue function will allow the measurement of tissue oxygenation and metabolisation in a broad variety of diseases and conditions (e.g. those discussed above).

It will be appreciated that the method of the invention has many advantages over prior art techniques. Prior to this invention, other workers analysed the OE-MRI signals by simplistic comparisons of the magnitude of signal change achieved at varying oxygen concentrations and/or the time taken for the signal to achieve maximum enhancement or the time for the signal to fall back to baseline. These simplistic approaches did not take into account the complex underlying interactions between the perfusion of oxygen by the blood, oxygenation of the tissues and metabolisation of the oxygen within the tissues.

A major advantage of the invention is that a clinician does not need to conduct any expensive and time consuming nuclear medicine tests, such as PET, to obtain data relating to tissue function. The method enables a person conducting the test to perform quick, relatively standard MRI (albeit the subject needs to wear a mask for supply of the first and further gases containing different concentrations of oxygen) and can very rapidly generate an image of the metabolic function, and in particular the metabolic consumption of oxygen, in a tissue area of interest.

DCE-MRI is known to be capable of generating parameters for $k^{trans}$, $v_e$ and $v_b$. These parameters are capable of providing measurements which are indicative of tissue function but their meaning is often different from the parameters produced according to the invention. $k^{trans}$ in DCE-MRI is a measure of the diffusion of a contrast medium from the blood plasma into the interstitium and is not used to estimate the diffusion capabilities of the tissue with regard to oxygen. In contrast, $K_{ox}$ according to the invention, is directly indicative of the diffusion of oxygen from the blood into the tissues. $v_p$ in DCE-MRI is a measure of the proportional volume of blood plasma in a voxel, because DCE-MRI contrast media is only present in the plasma and not the blood cells. In contrast, $V_b$ according to the invention is a measure of the proportional volume of blood in a voxel because there is oxygen present both in the plasma and the cells of the blood. $v_e$ in DCE-MRI is a measure of the proportional volume of interstitium in a voxel, because DCE-MRI contrast media cannot enter tissue cells and only resides within the interstitial spaces. $V_e$ according to the invention is a measure of the proportional volume of non-blood, including cells and interstitium, in the voxel because oxygen can enter the cells.

In each case, the difference in the type of measurement is rooted in the fact that the inventors have realised that contrast media used in DCE-MRI cannot cross into cells but oxygen (which is the contrast medium in OE-MRI) can cross into cells.

$M_{ox}$, according to the invention, is a measurement of metabolic consumption of oxygen within the tissues. It has not previously been possible to measure metabolic consumption via DCE-MRI due to the fact that artificial contrast media used in DCE-MRI are not consumed by any metabolic process. A marked advantage provided by the invention is therefore provided in the use of compartmental modelling or OE-MRI data to deliver measurements indicative of metabolisation of oxygen, a biological process which it has not previously possible to measure using either DCE-MRI or OE-MRI.

It should be noted that the concept of a compartmental model applied to imaging of tissue function is also applicable to other gases or aerosols that may be breathed by the patient and that cause a subsequent change in the signal observed in tissues of an area of interest. In particular, gases or aerosols which might be consumed as part of a metabolic process within the tissue area of interest would be suitable to produce data to which a compartmental model could be applied.

It will be appreciated that the use of a compartmental model, in conjunction with measurements of the concentration of oxygen in the tissue area of interest and an input function, allows the derivation of physiological parameters that have values that are independent of the scanning machine or data acquisition method (although it is acknowledged that these factors may affect the quality of the derived parameters). This is an advantage over methods that seek to measure oxygen enhancement ratios or wash-in rates based on NMR signal or $T_1$ values, each of which can be dependent upon the choice of field strength, the nature of the gas or aerosol, and NMR data acquisition technique.

A further advantage of using oxygen as a contrast agent is that it is non-toxic and requires no specialist preparation beyond the provision of a supply of pure oxygen. Other contrast media, such as those used in DCE-MRI, are often toxic and/or may even artificially influence t normal tissue function or metabolism. This may represent a particular problem in a subject already rendered vulnerable from an illness. In addition, a contrast medium introduced into a subject must be removed by the kidneys which, if they are not functioning correctly, may fail under the added strain. These factors can make the use of such contrast media unacceptable in circumstances in which an imaging subject is particularly vulnerable and/or is suffering from certain kidney conditions.

Furthermore, other possible contrast media that could be used in a compartmental model are generally of a specialist nature (for example gadolinium-based aerosols), making them a less practical option than oxygen. Additionally, oxygen may be breathed comfortably for many minutes without any practical or physiological complications. Other possible media (for example gadolinium-based aerosols) are generally limited to a single breath administration, which would limit their practical utility.

It will therefore be appreciated (e.g. in view of the issues discussed above) that the use of Oxygen as a contrast medium offers many advantages.

According to a second aspect of the invention there is provided a computer apparatus for generating data concerning tissue function, the apparatus comprising:
  a memory storing processor readable instructions; and
  a processor configured to read and execute instructions stored in said memory;
  wherein said processor readable instructions comprise instructions controlling said processor to apply the algorithm defined in the first aspect of the invention to tissue image data.

The apparatus according to the second aspect of the invention may comprise computational hardware and a display device required to calculate and display the outputs following the application of the algorithm. The hardware and display device may either be separate entities to the scanning device used in the method (e.g. an MRI scanner) or may be integrated within the scanner, as is the case for many biomedical digital imaging systems such as an MRI scanner. Therefore the computer apparatus may be part of a scanning apparatus.

It will be appreciated that computer software may apply the algorithm required to fit the model to the raw OE-MRI data and convert the output parameters to histograms or maps of tissue function, or to regional average values. Such histograms and maps are routinely generated for MRI. The manipulation of OE-MRI data with such software has the advantage that data from large numbers of voxels can be quickly manipulated, without user input, to provide a detailed image of function across the whole of a subject or a region thereof.

The algorithm of the invention may be embodied within computer software and may be implemented using a computational hardware and display device that is separate to the imaging device or integral to it. Such software represents a further aspect of the invention and according to a third aspect of the invention there is provided a carrier medium carrying computer readable program code configured to cause a computer to carry out a method of applying an algorithm as defined in the first aspect of the invention.

It will be appreciated that a computer program embodying the invention may be provided in any desirable manner. Such a computer program in any form represents a further aspect of the invention and according to a fourth aspect of the invention there is provided a computer program configured to cause a computer to carry out a method of applying an algorithm as defined by the first aspect of the invention.

Software according to the fourth aspect of the present invention may be provided in any desirable programming language including Java™ (Sun Microsystems, Inc. 901 San Antonio Road Palo Alto, Calif. 94303, USA), C++ (One Microsoft Way Redmond, Wash. 98052-6399, USA) or Matlab (The MathWorks, Inc. P.O. Box 845428 Boston, Mass., USA).

A user of software in accordance with the present invention would preferably obtain the software and install the software on an appropriate computer system which is configured to receive suitable MR image data, such as OE-MRI data.

Embodiments of the invention will now be further described, by way of example only, with reference to the following example and figures in which:

FIG. 1: illustrates a two-compartment model for transfer of oxygen in tissues using OE-MRI: The first compartment is the blood with a dissolved oxygen concentration $C_b$ which is proportional to the gaseous partial pressure concentration $P_AO_2$. A constant $K_{ox}$ describes the rate of diffusion to and from the second compartment comprising the tissues and interstitium. Oxygen is consumed by metabolic processes within the second compartment at a rate defined by the metabolic consumption rate $M_{ox}$.

Figure 2:
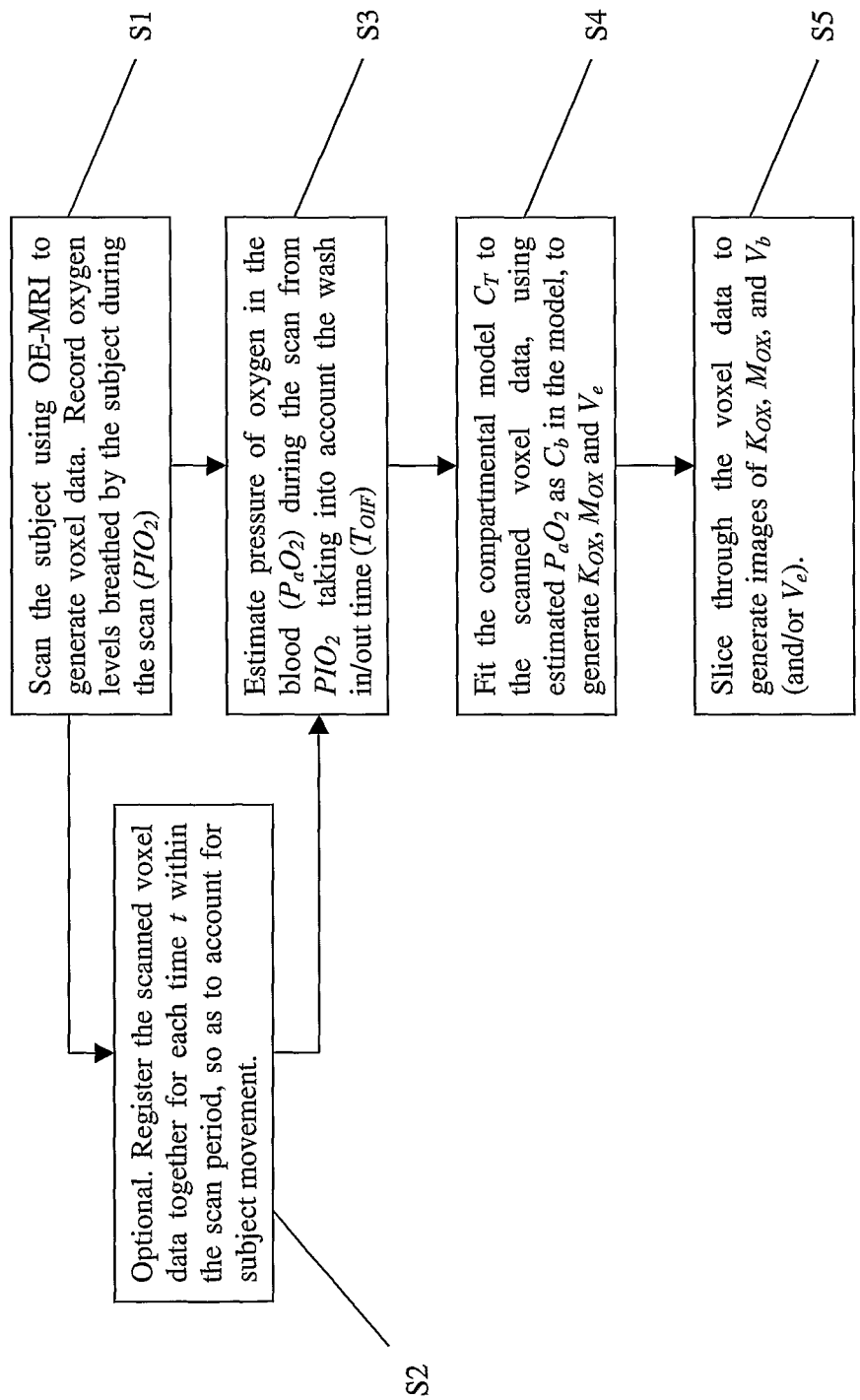

FIG. 2: depicts a flow chart representing a methodology according to an embodiment of the invention.

Figure 3:
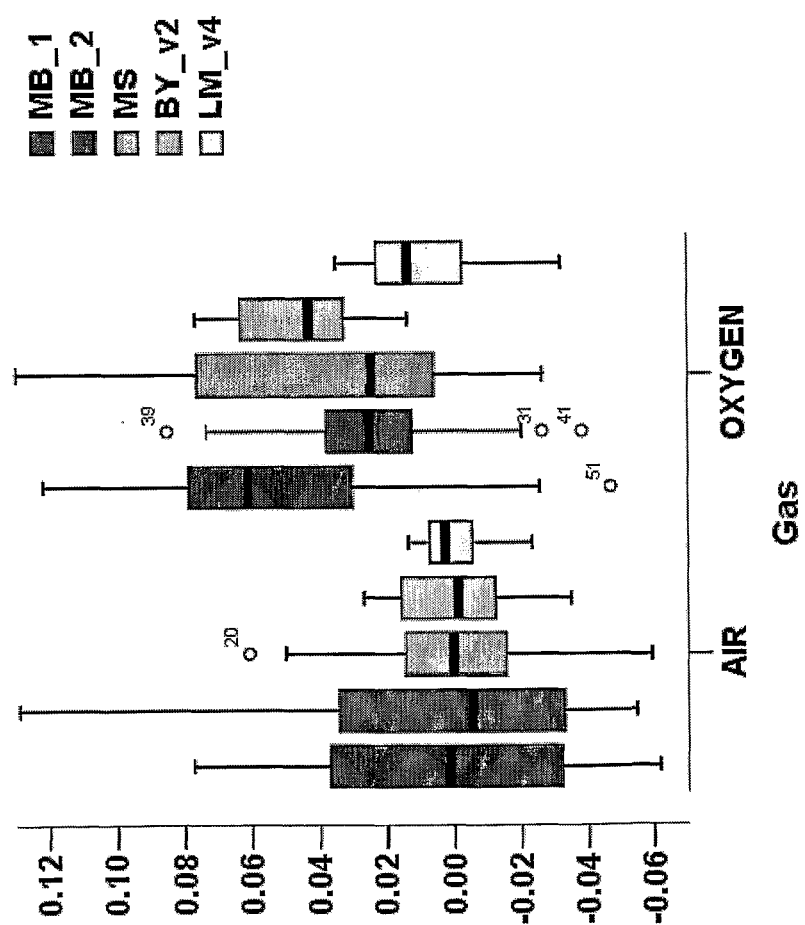

FIG. 3: Box-plot showing significant $\Delta R_1$ in 4 patients (Patient 1 had two tumours). Outliers are represented by circles (○).

Figure 4:
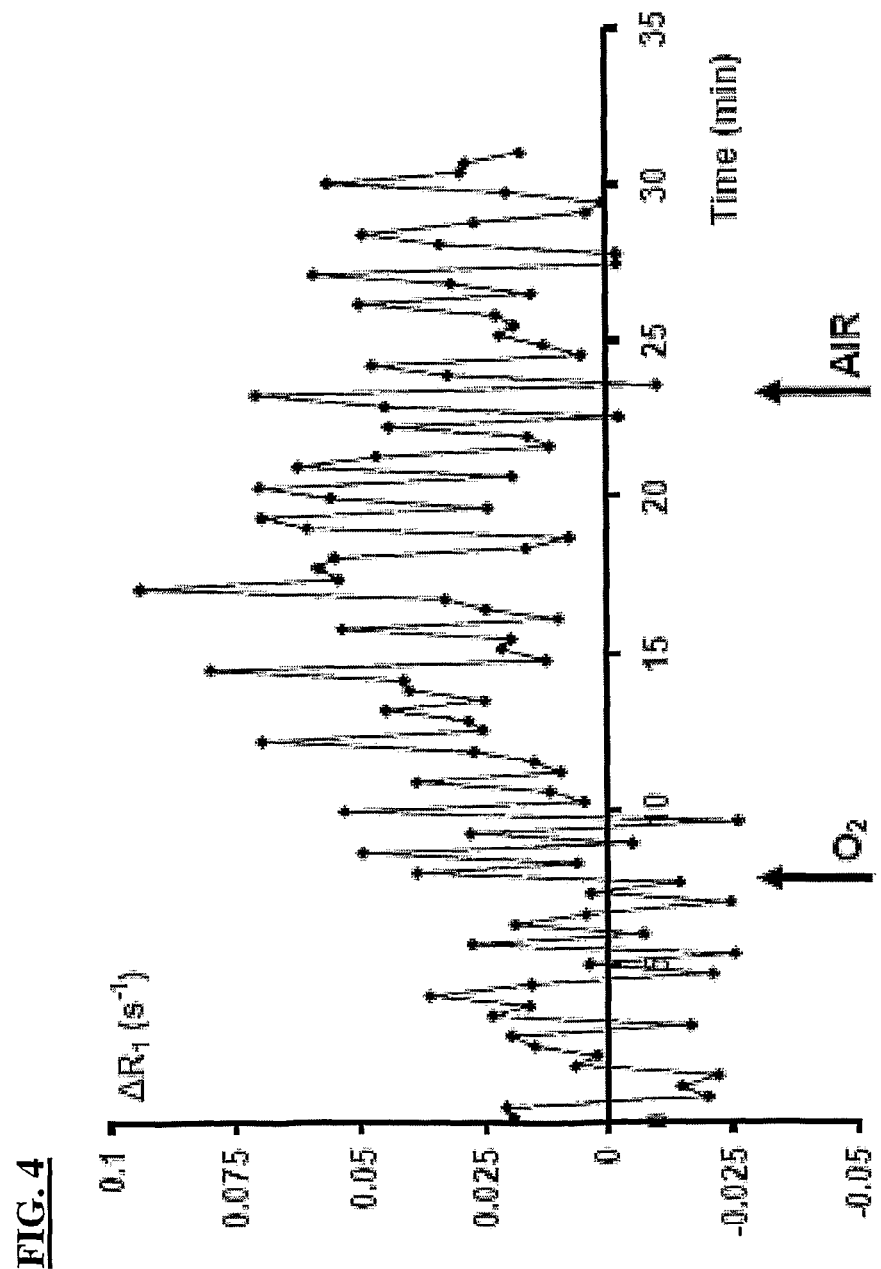

FIG. 4: Group averaged $\Delta R_1$ in 5 patients with 7 tumours. Switch to breathing 100% oxygen (O2) and medical air (Air) are indicated by arrows.

FIG. 5: Patient demographics and $\Delta R_1$ on inhalation of 100% oxygen. Mean $\Delta R_1$, 95% confidence intervals and p values are displayed.

Figure 6:
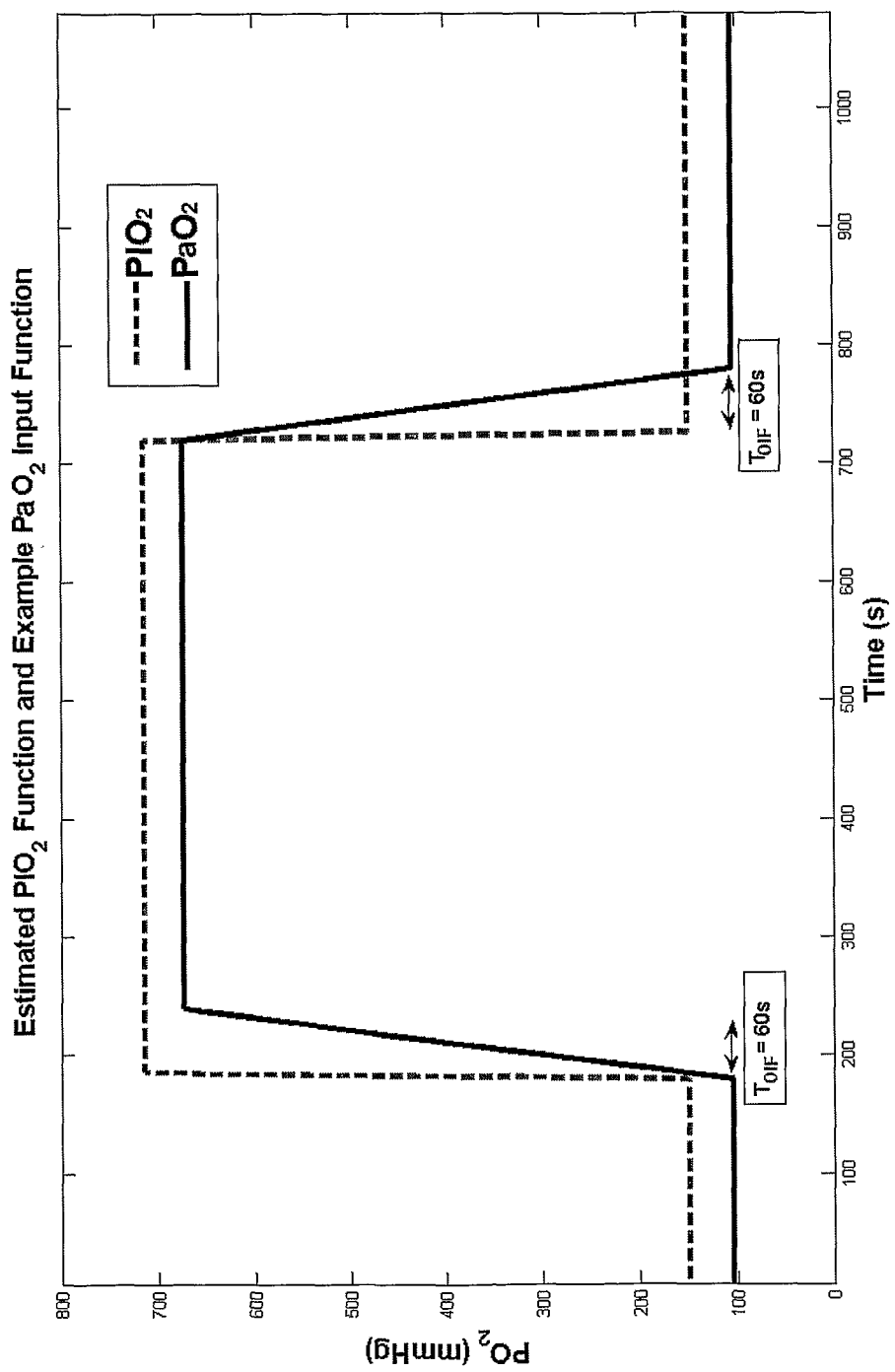

FIG. 6: A graph of the estimated change of arterial pressure of oxygen $P_aO_2$ to input oxygen pressure $PIO_2$, with $T_{OIF}$ defined.

Figure 7:
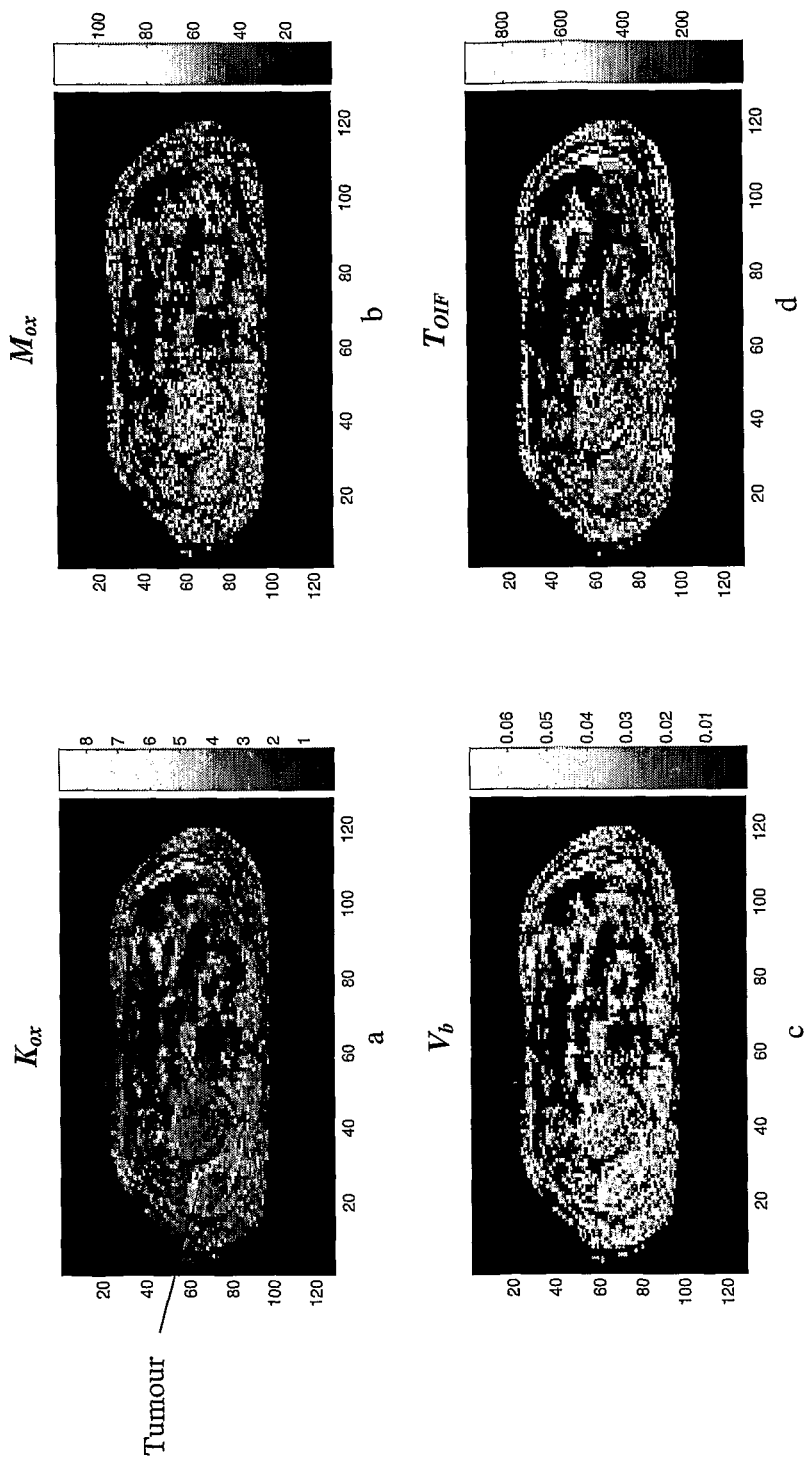

FIG. 7: Images showing parameter maps for parameters: (a) $K_{ox}$, (b) $M_{ox}$, (c) $V_b$ and (d) $T_{OIF}$ calculated according to the invention.

Figure 8:
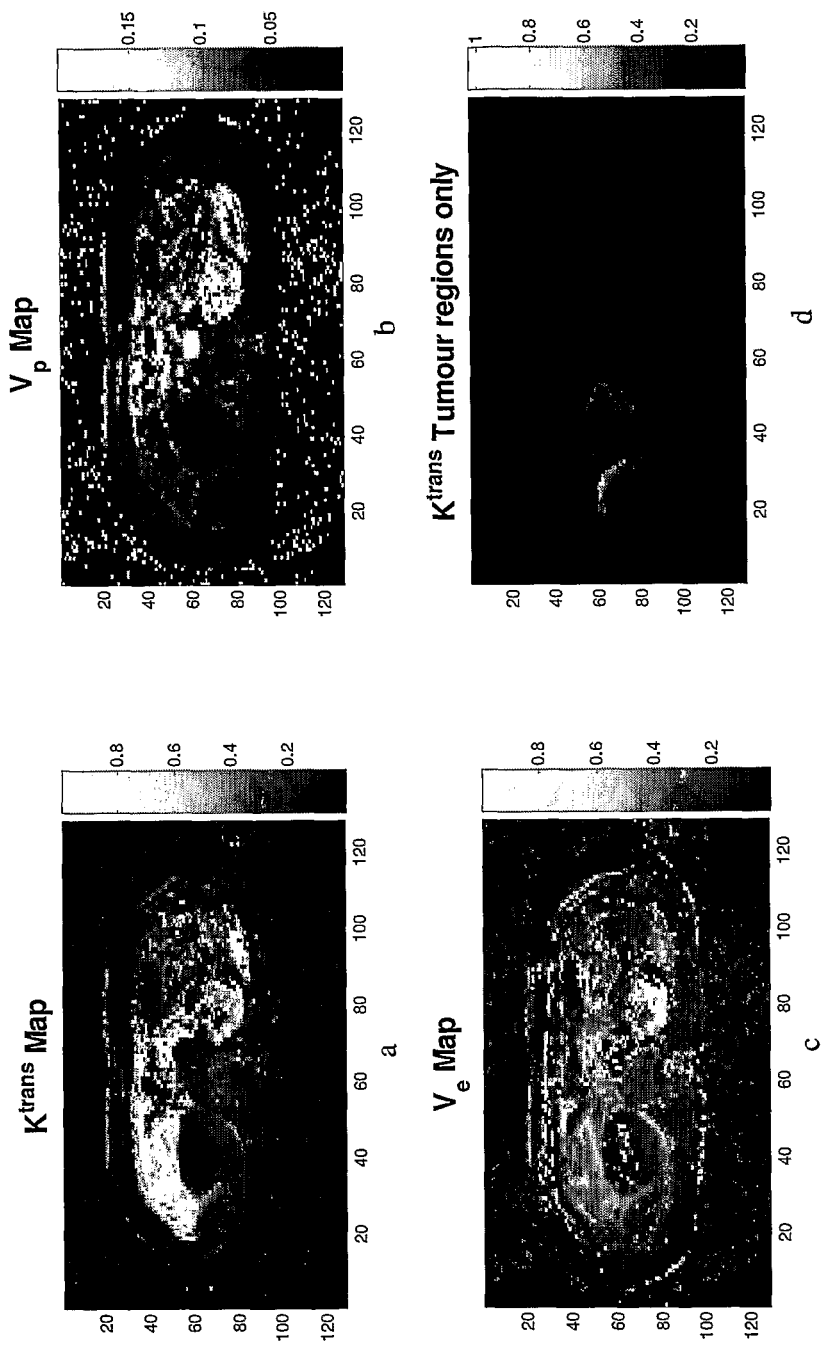

FIG. 8: Images showing parameter maps for parameters: (a) $k^{trans}$, (b) $v_p$, (c) $v_e$ and (d) $k^{trans}$ for the tumour region only; measured by DCE-MRI for comparative purposes.

Figure 9:
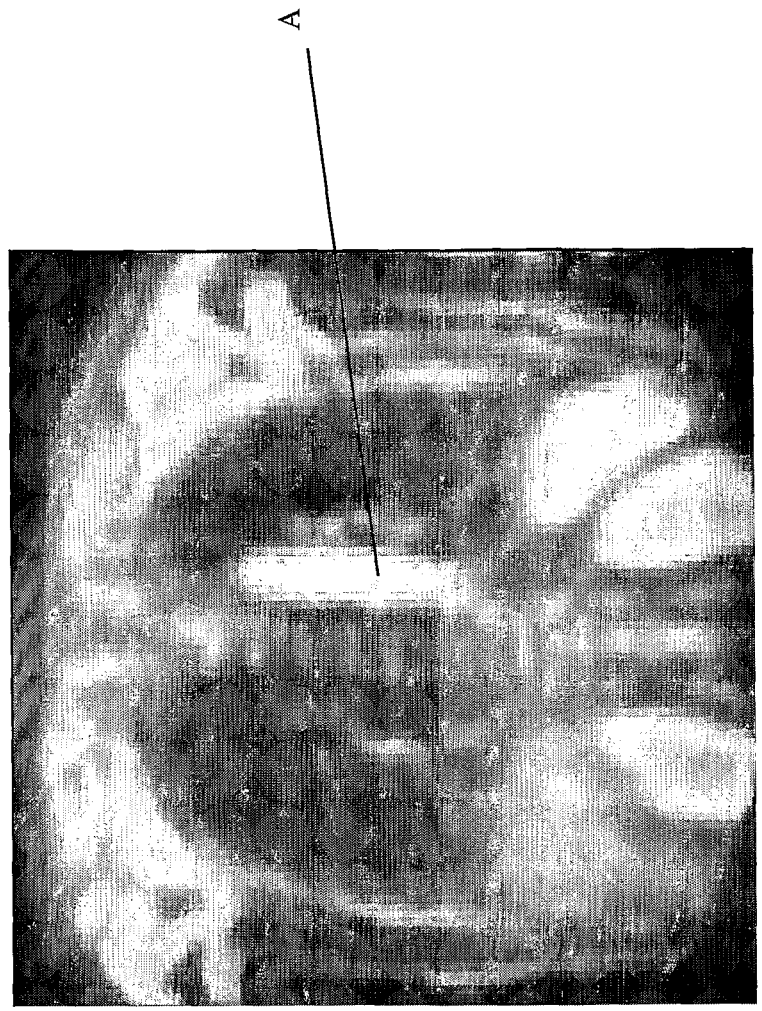

FIG. 9: Image showing the mean of 30 images of a subject breathing medical air with TI=217 ms clearly showing the aorta (labeled A).

Figure 10A:
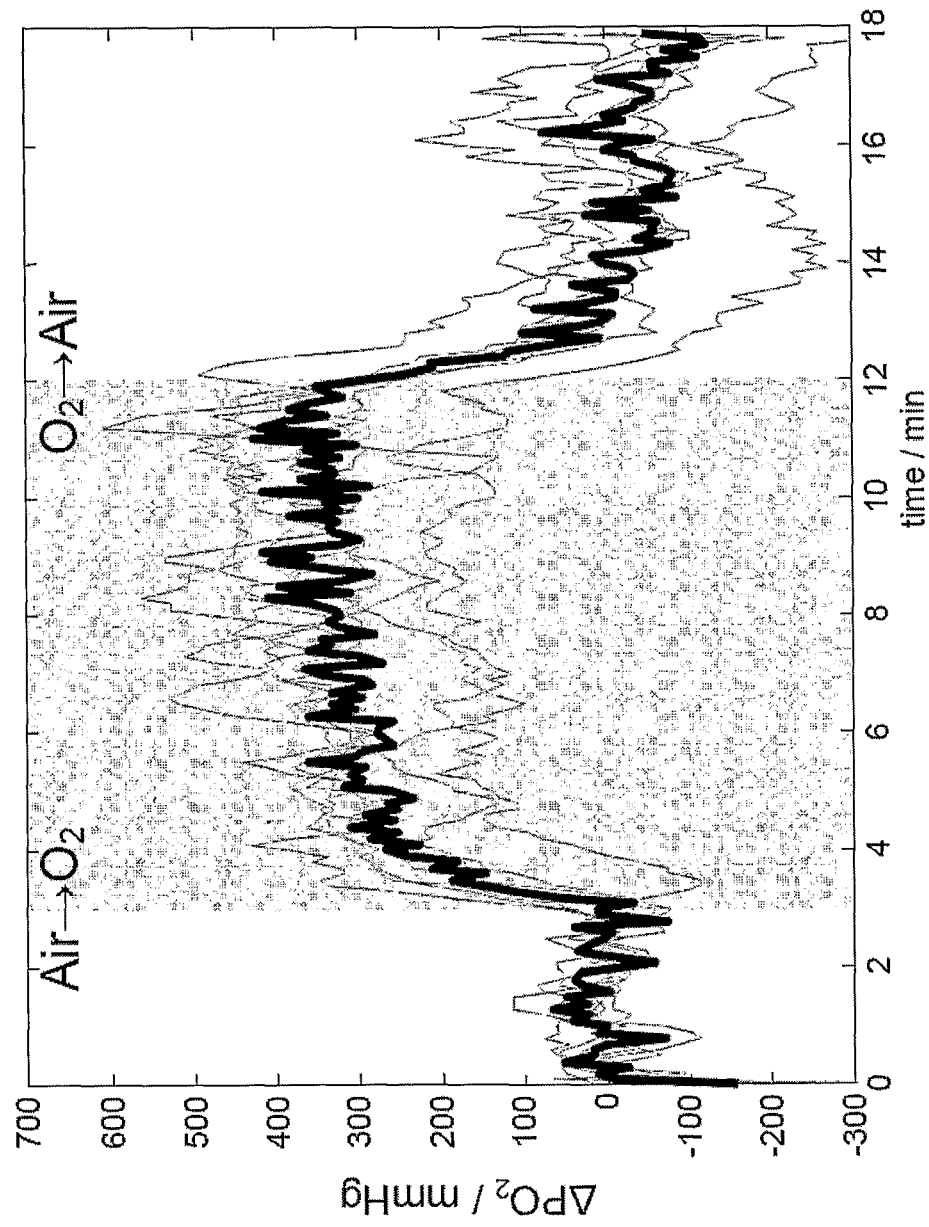

FIG. 10A: A graph showing $\Delta PO_2$ as a function of time for smokers plotted for each subject (thin lines), with the mean over all subjects shown as a single thick line.

Figure 10B:
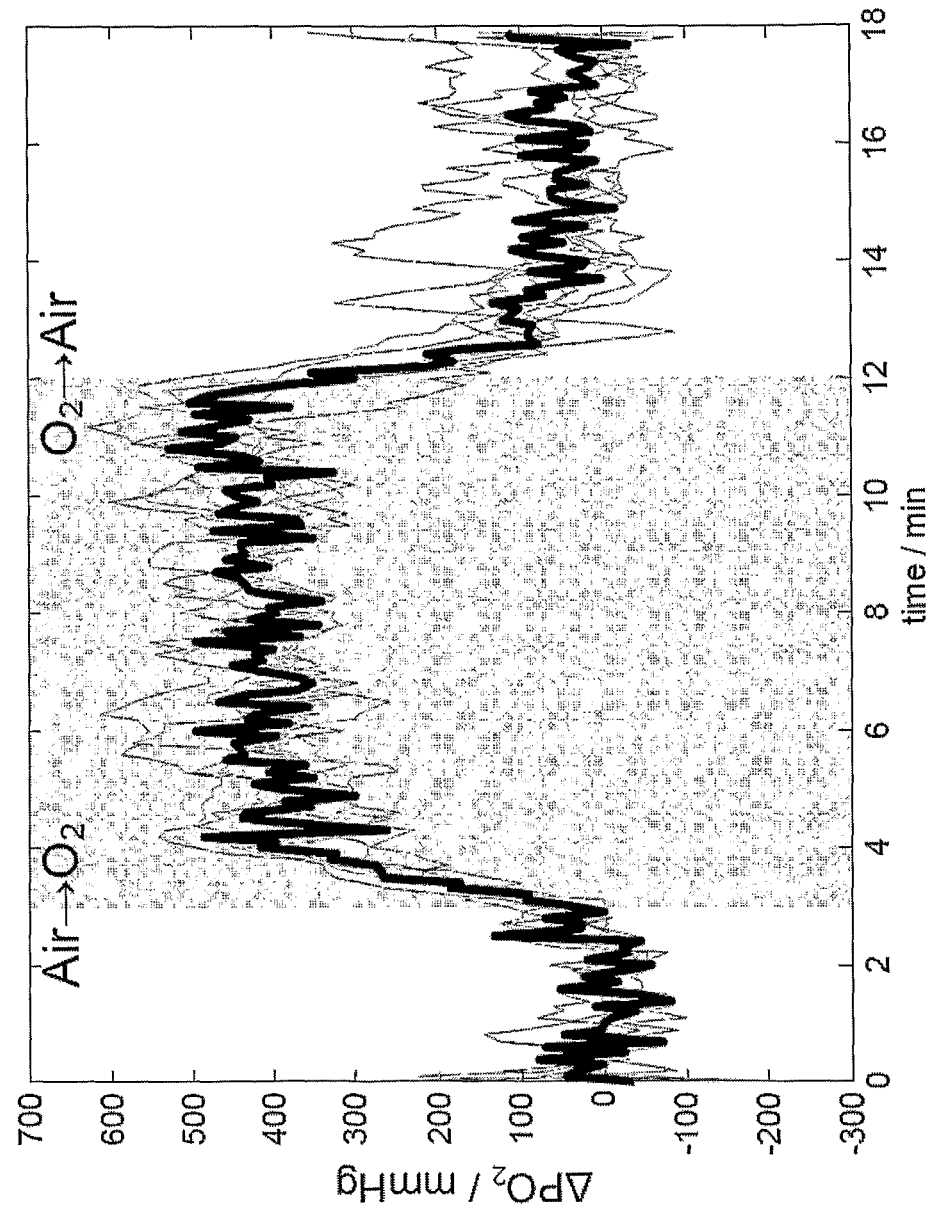

FIG. 10B: A graph showing $\Delta PO_2$ as a function of time for never-smokers plotted for each subject (thin lines), with the mean over all subjects shown as a single black line.

According to an embodiment of the invention, the methodology set out in the flow chart of FIG. 2 is followed. Tissues of a subject are scanned using OE-MRI and the data generated from the OE-MRI is used as an input to a compartmental model to produce clinically significant measures of tissue function within the subject.

In step S1, a patient is imaged using magnetic resonance imaging (MRI) during a period in which the patient first breathes air at a concentration ($PIO_2$) of approximately 21% $O_2$, then a gas comprising a higher $PIO_2$ such as 100% $O_2$ and then subsequently returns to breathing air. A graph of $PIO_2$, i.e. the concentration of $O_2$ breathed by the subject, over the time period of the scan therefore follows a top hat function, as shown by the dashed line labelled $PIO_2$ in FIG. 6. The MRI process, which is known in the art, produces a sequence of time dependent values for each of a field of voxels within a three dimensional region in the subject. Each sequence of values relates to a sequence of $T_1$ measurements made by the MR scanner in a voxel for each time t during the time period of the scan. Each value therefore gives an indication of the total concentration of oxygen in a voxel at a time t.

In step S2, the three dimensional field of voxels for each time point are registered together so that, if the subject moved during the time period of the scan, these movements can be corrected out of the data produced by the scan. Thus, once registration has been completed, and movements have been accounted for, it can be said that corresponding voxels in the field of voxels for each time t relate to $T_1$ measurements taken from the same physical location within the subject. It will be appreciated that registration is an optional component of the invention. For example, when scanning areas of a subject which can be kept immobile, registration is not necessary. Even in cases in which there is movement in the subject, the invention is practicable without the need to register the fields of voxels together, although registration may be used to improve the quality of the voxel data for some tissues.

In step S3, an estimate of the concentration of oxygen in the blood of the subject ($P_aO_2$) is made using the known concentration of oxygen breathed by the subject ($PIO_2$). This estimate is made from $PIO_2$ using an assigned value for the wash in and wash out time for the increased level of oxygen in the blood ($T_{OIF}$). The value of $T_{OIF}$ is estimated from well known physiological averages. It will be appreciated, however, that the value of $P_aO_2$ may be directly or indirectly measured in a variety of ways. One way, which uses OE-MRI data of the aorta, is set out below in example 4.

In step S4, the compartmental model derived above in equations (I) to (V) is fitted to the data (i.e. the $\Delta R_1$ values) for each voxel generated in step S1. The model output $C_T$ (i.e. $PO_2$) represents a function, which is defined in equation (V), controlled by the parameters $C_b$, $K_{ox}$, $M_{ox}$ and $V_e$. $C_b$, which is the concentration of oxygen in the blood compartment of the model, may be directly inferred from the pressure of oxygen in the blood, $P_aO_2$ defined in step S3 (for example by assuming that $C_b$ is equal to $P_aO_2$). This inferred $C_b$ is therefore an input to the compartmental model.

It will be appreciated that fitting a function to a sequence of data can be achieved by a number of methods, however the preferred method of fitting is to use a non-linear least squares approach such as the Levenberg Marquardt algorithm.

Fitting the model to the data for each voxel over the time period of the scan provides a value for each of $K_{ox}$, $M_{ox}$, and $V_e$ for each voxel which, when fed into the model produce a function for which there is the least squared error, or difference, from the OE-MRI data for that voxel. Thus, the result of step S4 is a set of parameters ($K_{ox}$, $M_{ox}$ and $V_e$) relating to each voxel in the three-dimensional field of voxels over the time period of the scan. In the following examples, it is established that the parameters $K_{ox}$, $M_{ox}$ and $V_e$ are clinically useful in that they are indicative respectively of the diffusion capability, the metabolisation capability and the partial volume (per voxel) of non-blood matter in the subject. The parameter $V_b$ is then calculated from $V_e$ as set out above in relation to equation (II).

In step S5, images are produced from the field of voxels by defining a two-dimensional plane which slices through the field of voxels. Voxels which lie on the plane are included in an image formed on the plane. Thus, images can be formed for each of the parameters ($K_{ox}$, $M_{ox}$ and $V_e$). Example images generated for each of the parameters in example 2 are shown in FIG. 6. It will be appreciated that other representations of the data may readily be constructed from the model outputs including three-dimensional polygonal representations or volumetric representations. The data may also be represented numerically or in graphs, or indeed in any format in which the data provides readily accessible diagnostic information.

In particular, values of $M_{ox}$ or $K_{ox}$ may be displayed in the form of comparative tables, graphs or images so as to compare metabolic consumption or diffusion of oxygen in tissues during two or more different scans of the same subject or between two or more different subjects. It will be appreciated that, in this manner, valuable diagnostic and prognostic information may be gleaned from the results of the compartmental modelling algorithm according to the invention.

EXAMPLE 1

This example describes a test in which OE-MRI scan data was collected from a number of subjects. This data is of a suitable nature to be used in accordance with the invention. In accordance with the invention, a compartmental model could be fitted to this data so as to produce parameters (such as $K_{ox}$, $M_{ox}$ and $V_b$) relating to tissue function. An example of the use of such data in accordance with the invention is provided in example 2.

Here we describe the oxygen-induced modulation of tumour longitudinal relaxation rate ($R_1$)—an effect previously described in normal tissues (R A Jones et al., (2002) MRM 47: 728-35; and JP O'Connor et al., (2007) MRM 58: 490-6)—that is distinct from the blood oxygenation level dependent (BOLD) technique. We evaluated the technique in a cohort of patients with advanced carcinoma.

(a) Methods

Ethical approval was obtained. Patients were imaged on a Philips Intera system (Philips Medical Systems, Best, Netherlands) at 1.5 tesla. Subjects inhaled medical air (21% oxygen) followed by 100% oxygen and then a second phase of medical air at 15 l/min through a non re-breathing circuit with reservoir mask. Initial $T_1$-weighted and $T_2$-weighted anatomical sequences were performed to delineate the tumours. Only lesions of ≥3 cm in-plane and present on at least 3 slices were included.

The whole body transmit/receive coil was selected for transmission and reception. Series of 3D $T_1$-weighted fast field echo images were acquired (TR 3.5 ms, TE 0.9 ms, a=2°/8°/17°, one average, FOV of 375 mm, matrix 128×128, 4 mm slice thickness) to estimate tissue $T_1$. 10 cm volumes were selected in each patient to cover the tumour. Measurements were acquired during gentle breathing without breath holding. Twenty four baseline measurements were collected while breathing medical air, followed by 48 on 100% oxygen, and then a further 24 back on medical air. Total acquisition time for each $T_1$ measurement was 19.5 s. Total imaging time was 31 min 12 s. Finally, 0.1 mmol/kg of Omniscan (Amersham Health, Amersham, UK) was administered intravenously through a power injector at 3 ml/s. Dynamic contrast-enhanced MRI was performed (TR 4.0 ms, TE 0.82 ms, a=20°, identical average, FOV, matrix and slice thickness as for gas inhalation protocol) following fast field echo calculation baseline of $T_1$ with flip angles 2°/10°/20°/30° and 4 NSA. Temporal resolution was 4.97 s.

Image analysis was performed using a voxel-by-voxel fitting process with in-house software. Tumour volumes were identified from the $T_1$-weighted and the $T_2$-weighted anatomical images and a volume of interest (VOI) was drawn to encompass the entire lesion. Change in the longitudinal relaxation rate ($\Delta R_1(t) = R_1(t) - R_1(air)$) was calculated for each time-point (as described in JP O'Connor et al., (2007) MRM 58: 490-6). $\Delta R_1$ is proportional to the change in oxygen concentration at time point (t), with the pconstant of proportionality being $r_1$, the longitudinal relaxivity constant for oxygen. $R_1(t)$ is the $R_1$ value at each time point and $R_1(air)$ is the mean baseline $R_1$ value (while breathing air). Significance of measured change in $R_1$ was tested by a one-way analysis of variance in SPSS 13.0. IAUC and $K^{trans}$ were calculated using the extended Tofts model with an assumed arterial input function (as described in G J Parker et al., (2006) MRM 56: 993-1000) and correlated with oxygen-induced $\Delta R_1$ using Spearman's rho.

(b) Results

Five patients with advanced solid tumours were recruited (all female; mean age 62.6 years). The imaging protocol was well tolerated by all subjects. In total, seven lesions were identified. Mean $\Delta R_1$ values for each tumour of between 0.0087-0.0526 s$^{-1}$ were measured when breathing 100% oxygen and this change was statistically significant in five lesions (FIGS. 3 and 5). The $\Delta R_1$ returned to that of baseline on switching back to medical air in only one tumour (Pt 1 Tumour 2; p=0.02). Group analysis showed clear elevation of $\Delta R_1$ during oxygen inhalation (p<0.001) and a non-significant reduction in $\Delta R_1$ towards baseline values when patients returned to breathing medical air (p=0.117) (FIG. 4). Patient demographics and tumour details are summarised in Table 1. There was no significant correlation between the magnitude of oxygen-induced $\Delta R_1$ and tumour median IAUC or $K^{trans}$.

(c) Discussion

Image contrast in $R_1$ mapping following inhalation of hyperoxic gas is due to the paramagnetic effect of dissolved molecular oxygen in the arterial blood plasma and tissue fluid. This study is the first to describe the effect in human tumours and reports significant $\Delta R_1$ when subjects switch from medical air to 100% oxygen in four patients with advanced epithelial ovarian carcinomas. Modest but non-significant $\Delta R_1$ were detected in two liver metastases in a patient with gastric adenocarcinoma. While arterial blood flow is likely to be an important factor contributing to signal change, the measured $\Delta R_1$ was independent of the tumour blood flow estimated by both IAUC and $K^{trans}$, suggesting that oxygen-induced $\Delta R_1$ is likely to be a composite measure of oxygen delivery, diffusion and metabolism. In general, the protocol was well tolerated and produced measurable signal change with an acceptable signal-to-noise ratio. These preliminary results are encouraging and suggest that modulation of tumour $R_1$ may produce novel biomarkers of oxygenation status that merit further investigation.

Thus, this example shows that the difference in oxygenation of tumours between periods in which the subject breathes two different partial pressures of a paramagnetic gas (oxygen) are measurable through OE-MRI. This data is therefore suitable for application to the compartmental modelling algorithm in a method according to the invention.

EXAMPLE 2

This example demonstrates fitting a compartmental model to OE-MRI data such as that generated in example 1. The results of the application of the exemplary compartmental model are described with reference to standard parameters generated from DCE-MRI, which is an accepted medical imaging modality with proven diagnostic and prognostic capabilities.

The data acquisition methods described in the methods section of the first example were applied to a subject known to be suffering from a tumour in order that the utility of the methods of the invention could be validated. Results generated according to the methods of the invention were compared with those obtained using a conventional imaging technique (DCE-MRI).

(a) Methods

The data acquired from the scan of the further subject, which was conducted in accordance with the scans described above in relation to the first example, was used as input data to a fit of the compartmental model described above in relation to equations (I) to (V).

The dissolved oxygen induces an increase in $R_1$ (as described above) of the surrounding water protons that is measured by an increased signal in the $T_1$-weighted images. As set out above, the relationship between $R_1$ and the local oxygen concentration was measured by Heuckel and Silvennoinen in blood with varying haematocrit. An approximate average from their experiments for a typical haematocrit of 0.41 is $r_1 = 4 \times 10^{-4}$ s$^{-1}$ mmHg$^{-1}$. This factor can be used to convert $R_1$ to PO$_2$ by dividing $R_1$ by $r_1$. The resulting values of PO$_2$ may then be input to the model set out in equations (I) to (V), as $C_r$.

Data to be input as $C_b$ was generated by applying a conversion factor to values for the breathed pressure of oxygen (PIO$_2$) as outlined in FIG. 6. FIG. 6 shows an estimated arterial pressure of oxygen (P$_a$O$_2$) against the known input (i.e. breathed) pressure of oxygen (PIO$_2$). It can be seen that after the input pressure of PIO$_2$ has been increased, the arterial pressure P$_a$O$_2$ increases accordingly, taking a time T$_{OIF}$ to increase to a maximum pressure. A subsequent drop in the pressure of oxygen breathed by the patient causes a drop in arterial partial pressure P$_a$O$_2$, and again the time taken for the arterial partial pressure to follow the change in input partial pressure PIO$_2$ is indicated by T$_{OIF}$.

It will be appreciated that direct measurements of P$_a$O$_2$ (e.g. see example 4) may also be used as an input for $C_b$.

(b) Results

The converted OE-MRI data (PO$_2$) and P$_a$O$_2$ data were input into equation (V) as $C_T$ and $C_b$ respectively and the Levenberg Marquardt non-linear least squares fitting algorithm was applied.

This enabled the inventors to generate data providing clinically useful information relating to $K_{ox}$, $M_{ox}$, $V_e$ and other parameters that can be presented as images of the scanned tissues of interest (see FIG. 7).

For the purposes of comparison, FIGS. 7 and 8 each show four axial views of the subject, labelled (a) to (d). Each image is produced from data taken from the same area within the subject and shows values from both healthy tissue and tumorous tissue. FIG. 7 shows results of OE-MRI using the compartmental model as set out above with reference to equations (I) to (V). FIG. 8 shows standard values obtained from DCE-MRI of the same subject.

FIG. 7 shows tissue maps for a number of parameters which have been calculated from the compartmental model for the subject. It can be seen in FIG. 7a, which shows values of $K_{ox}$, that a tumour within the subject is visible as a relatively bright oval shape on the left side of the image. This indicates that the oxygenation of the tumour tissue is better than the surrounding tissue. An upper edge portion of the tumour is particularly visible, being brighter in shade than the surrounding tumorous and non-tumorous tissue.

FIG. 7b shows the values for $M_{ox}$, or metabolic consumption of oxygen, for the subject at the same location. Again, the image is brighter in the region of the tumour, which indicates that the tumour is consuming oxygen at a higher rate than surrounding tissue. The brighter upper edge portion of the tumour is again shown, which indicates that metabolic activity in this region is high. This indicates a potential direction of new growth for the tumour. It would not be possible by any other known method to directly observe the consumption of oxygen by a tumour in this way and the inventive method therefore provides a significant advantage in directly assessing the likely future growth of a tumour. This is a parameter which cannot be produced by DCE-MRI since the visible contrast media used in DCE-MRI are not suitable for metabolic consumption. As a result, $M_{ox}$ is a result generated by this exemplary embodiment of the present invention which can provide diagnostic information which was not previously available to the diagnostician.

FIG. 7c shows the values of $V_e$, or the proportion of tissue to blood, across the same region of the subject shown in FIGS. 7a and 7b. FIG. 7c shows that the tumour has more blood within it than its surrounding area. The high blood concentration in the tumour can be used to detect the tumour and also to characterise its function in that a tumour receiving a greater blood flow is likely to be more metabolically active. Also, many treatments of tumours focus on reducing blood flow to the tumour and calculation of this value using the present invention would be useful for evaluating the success of such a therapy.

FIG. 7d shows the $T_{OIF}$ lag time for maximum concentration of oxygen within the tissues of the subject. It can be seen from FIG. 7d that the tumour appears different to the surrounding tissue, although it is also clear that this image alone would not be as effective for the detection and characterisation of tumours. Less accurate values for wash-in and wash-out times in tissues have previously been calculated for OE-MRI of tumours.

FIGS. 8a-8c show values of $K^{trans}$, $V_p$ and $V_e$ which are standard values generated by DCE-MRI scans. $k^{trans}$ cannot be considered to be identical to $K_{ox}$, on the basis that $k^{trans}$ in DCE-MRI is a measure of the diffusion of an artificial contrast medium from the blood plasma into the interstitium, while $K_{ox}$ according to the invention is a measure of the diffusion of oxygen from the blood into the tissues. Similarly, $v_p$ in DCE-MRI is a measure of the proportional volume of blood plasma in a voxel, while $v_b$ according to the invention is a measure of the proportional volume of blood in a voxel. $v_e$ in DCE-MRI is a measure of the proportional volume of interstitium in a voxel, while $v_e$ according to the invention is a measure of the proportional volume of non-blood, including cells and interstitium, in the voxel.

In each case, the difference in the type of measurement is rooted in the fact that the artificial contrast media used in DCE-MRI cannot cross into cells but oxygen can. Thus, $v_p$ is not a measure of the whole blood (including haemoglobin) but only blood plasma, because DCE-MRI contrast media may not enter red blood cells; $v_e$ (for DCE-MRI) is only a measure of the interstitium because contrast cannot enter cells.

$k^{trans}$ is a measure of "leakiness" in a blood vessel, i.e. the ability of blood vessels to diffuse contrast media from the plasma into the surrounding interstitial spaces. $K_{ox}$, however, is a measure of the capability of a blood vessel to diffuse oxygen from the blood into the surrounding tissue. It will be appreciated that measured $k^{trans}$ cannot be used to characterise the ability of a blood vessel to diffuse oxygen from the blood into local tissue. $K_{ox}$ therefore represents a measurement which cannot be measured by DCE-MRI.

$M_{ox}$, according to the invention, is a measurement of metabolic consumption of oxygen within the tissues. FIG. 8 shows no comparable image generated by DCE-MRI. This is because it has previously not been possible to measure metabolic consumption via DCE-MRI due to the fact that artificial contrast media are not consumed. An advantage provided by the invention is therefore the ability to measure a biological process which it has not previously possible to measure.

The values of $M_{ox}$, $K_{ox}$ and $V_e$ determined according to the invention cannot be directly measured from OE-MRI data and must therefore be inferred by fitting a compartmental model to values (e.g. of $PO_2$) which can be directly measured.

The method according to the invention of determining values for $M_{ox}$, $K_{ox}$ and $V_e$ is therefore advantageous in that measurements are obtained which cannot be obtained by DCE-MRI or by OE-MRI without the use of a compartmental model.

The images shown in FIG. 8 may be used to validate the findings of the compartmental model as shown in FIG. 7, since it is clear from FIG. 8 that a tumour exists and that is has the same dimensions as those depicted in the results of FIG. 7. However, the tumour shown in FIG. 8 appears to be dark in its centre. This is due to the lack of perfusion of the contrast medium used in DCE-MRI to the centre of the tumour, and to the fact that DCE-MRI is not able to characterise metabolic consumption since the contrast medium is not consumed by metabolic processes. FIG. 8d shows the $k^{trans}$ for the tumour region only, for clarity.

It is clear from FIG. 7 that it is possible to detect and visualise the tumour shown in those figures from any of the values of $K_{ox}$, $M_{ox}$, or $V_e$ but that the value of $M_{ox}$ is particularly useful both in detecting the tumour and in characterising the metabolic function of the tumour as different from the surrounding tissue. This shows that the invention provides clear benefits in the diagnostic and prognostic capability of OE-MRI and that these are potentially improvements of the diagnostic capability of DCE-MRI of the same patient.

EXAMPLE 3

In this example, the inventors implemented a compartmental model algorithm in accordance with an aspect of the present invention. The algorithm was implemented as software in Matlab script. The inventors packaged the Matlab script, which implements the compartmental model algorithm, for distribution on a compact disc.

The compact disc containing the software was given in confidence to an operative who was in possession of a 1.5 T Philips Gyroscan NT Intera MR scanner. The operative used the scanner, together with oxygen breathing apparatus widely available in medical environments, to perform an OE-MRI scan on a human patient according to the method described in the first example. The operative then used the software on the compact disc to analyse the data generated by the OE-MRI scan of the patient so as to characterise the patient's tissue function, in accordance with an aspect of the present invention.

The compartmental model generated values indicative of the patient's tissue function, including $K_{ox}$, $M_{ox}$ and $V_e$. The software displayed the values generated by the compartmental model in a number of ways, including as a series of graphs and tissue parameter maps. The data values, the graphs and the tissue parameter maps were used by a medical professional to analyse the metabolic tissue function of the patient and diagnose illness in the patient. The sensitivity of the model to the function of relatively small tissue areas of interest within the patient allowed the medical professional to diagnose local areas of abnormal oxygen metabolisation within the tissues and to target therapy accordingly. The use of OE-MRI to generate the data that was then input into the compartmental modelling software was particularly new and interesting in that the medical professional was able to directly analyse the function of tissues in relation to oxygen metabolisation. This direct analysis has not been possible before the present invention.

EXAMPLE 4

The parameter $C_b$ (concentration of oxygen in the blood compartment) in the compartmental model of equation (V) is an input to the model which, in example 2, is derived directly from an estimate of the partial pressure in blood ($P_aO_2$). $P_aO_2$ is, in turn, estimated from the partial pressure of oxygen breathed by the subject ($PIO_2$) in consideration of the wash in and wash out times of the blood ($T_{OIF}$), which are also estimated. If, however, $P_aO_2$ can be directly measured then these estimates are no longer needed as inputs to $C_b$. This example represents a demonstration that $P_aO_2$, and consequently $C_b$, can be directly measured from OE-MRI data scanned from the aorta region within a subject. It will be appreciated that the data which results from this example may readily replace the estimated $P_aO_2$ data which is used as an input to the $C_b$ parameter of the compartmental model of example 2. It will further be appreciated that this exemplary method of measuring $PO_2$ may advantageously be combined with the estimations of example 2, particularly but not exclusively with a view to correcting errors in measurement of $PO_2$ from the aorta.

In this example, the input function representing the change of arterial pressure of oxygen $P_aO_2$, which is modelled from estimations in examples 1 and 2, was measured directly from MRI data. This could be directly input to the model by inputting the measured $P_aO_2$ into the model parameter $C_b$ in place of an estimated $P_aO_2$ such as that shown in FIG. 6.

(a) Methods

Twenty four subjects underwent dynamic OE-MRI at 1.5 tesla. Fourteen volunteers (7 smokers (S), 7 never-smokers (NS)) had their aorta in the field of view and were therefore selected for further analysis. Informed consent was obtained from all subjects. A 15 mm thick coronal slice was positioned posterially with a 44.5 cm×44.5 cm field of view, as shown in FIG. 8. This volume was imaged using an inversion-recovery turbo field echo sequence (TR/TE 2.2/1.0 ms, flip angle 5°, acquisition matrix 128×256 zero filled to 256×256) to acquire images throughout recovery from an initial non-selective inversion pulse (25 inversion times were used, shortest 74 ms with intervals of 143 ms), permitting a measurement of $T_1$. The acquisition was repeated continuously for 18 minutes, giving $T_1$ measurements at a time resolution of 6 seconds. The volunteers breathed medical air via a Hudson mask for the first 3 minutes, then the supply to the mask was switched to 100% oxygen. After a further 9 minutes, the supply was switched back to air for the remainder of the acquisition. Gas was delivered at 15 l/min.

A region of interest was marked for the aorta (labelled A in FIG. 9) and dynamic measurements of $T_1$ were extracted by fitting the Look-Locker signal equation (Henderson E, McKinnon G, et al. Magn Reson Imaging 1999; 17:1163-1171). Changes in $T_1$ due to inhalation of oxygen were converted to changes in partial pressure of oxygen in blood plasma ($\Delta PO_2$) using the relaxivity constant $r_1=2.49\times10^{-4}$ (Zaharchuk G, Busse R F, et al. Acad Radiol 2006; 13:1016-1024). The mean $\Delta PO_2$ in the plateau region of the dynamic curve (chosen as the region between 8 and 12 minutes) was recorded for each subject, and a Wilcoxon rank sum test was used to compare these values for smokers and never-smokers, testing the hypothesis that S had lower plateau $\Delta PO_2$ values than NS due to possible reduced oxygen exchange efficiency.

(b) Results

The regions of interest, i.e. the area of the images representing the aorta, contained a mean of 42±20 pixels. Mean baseline and plateau $T_1$ values were 1300±200 ms and 1200±100 ms for S and 1300±200 ms and 1100±100 ms for NS respectively. FIGS. 10A and 10B show $\Delta PO_2$ plotted as a function of time for each subject in the two groups, smoothed using a 5-point moving average. The bold line shows the mean time course over all volunteers (unsmoothed). The mean plateau value was 350±90 mmHg for S and 430±40 mmHg for NS (p=0.049).

(c) Discussion

In this small number of volunteers, the plateau $\Delta PO_2$ values showed a borderline significant difference between the two groups, with S showing lower plateau $\Delta PO_2$ values than NS. The standard deviation of the plateau $\Delta PO_2$ in S was double that in NS. Literature values for arterial blood gas measurements of $PO_2$ in normal volunteers when breathing air and 100% oxygen suggest that the expected $\Delta PO_2$ should be 490±20 mmHg (Floyd T F, Clark J M, et al. J Appl Physiol 2003;95:2453-2461), which is in agreement with our findings. Direct comparison with arterial blood gas sampling would be advantageous to validate the measurement and the study of more subjects will allow stronger conclusions to be drawn regarding any difference between S and NS.

These curves show that the gas delivery system used in OE-MRI is functioning as expected, and also give an indication of global lung function by showing how well the lungs are oxygenating the blood, although they do not provide information on haemoglobin transport. These measurements of arterial plasma oxygenation may readily be used as the input function to the compartment models of examples 1 and 2, or indeed any appropriate model of tissue function.

In conclusion, we have measured $T_1$ changes in the aorta for smokers and never-smokers due to breathing 100% oxygen, which, assuming a value for $r_1$, can be converted to a measurement of $\Delta PO_2$ (which, when measuring entirely in the aorta, is equivalent to $P_aO_2$) that is in agreement with literature values. These non-invasive measurements have potential in modelling of oxygen uptake in a wide range of tissues and also for modelling gas exchange in the lungs.

This represents a preferred method of determining the input $P_aO_2$ ($C_b$) to the compartmental modelling algorithm of the present invention.

The invention claimed is:

1. A method of characterising function of tissues of a body that receive oxygen from a vascular supply in a subject in need of such characterization, the method comprising:
    performing, with an imaging system having a computer and a processor, an Oxygen-Enhanced Magnetic Resonance Imaging (OE-MRI) on a tissue space associated with the tissue of interest,
    generating image data, with the imaging system, over a time period during which the subject inhales gases with at least two different partial pressures of oxygen, the image data providing information in respect of delivery of oxygen to a tissue and metabolic consumption of oxygen within the tissue; and
    applying, with the processor, a compartmental model algorithm to the image data generated to provide information on metabolic rate of oxygen consumption of the tissue, wherein the compartmental model algorithm includes a factor associated with metabolic consumption of oxygen in the tissue.

2. The method according to a claim 1 wherein the tissue space of interest includes a tumor.

3. The method according to claim 1, further comprising applying techniques to improve image registration to ensure that the imaging is conducted on the same voxel over time.

4. The method according to claim 1, wherein the method evaluates tissue function in humans or animals for either diagnostic or prognostic purposes or for therapeutic development.

5. The method of claim 1, further comprising dividing the tissue into a matrix of voxels and OE-MRI data is generated for each voxel.

6. The method of claim 5, wherein the OE-MRI data generated while the subject first inhales a first gas with a partial pressure of oxygen between 0% and 35% oxygen; then breathes a second gas with a partial pressure of oxygen between 45% and 100% oxygen.

7. The method of claim 6 wherein the first gas is air and the second gas is 100% oxygen.

8. The method according to claim 1 wherein the compartmental model algorithm is a two-compartment model based on physiological parameters for rate of delivery, diffusion and metabolisation.

9. The method according to claim 8 further comprising calculating with the compartmental model algorithm the combined oxygen concentration of a second compartment comprising tissue and interstitium ($C_e$).

10. The method according to claim 8 further comprising calculating with the compartmental model algorithm the fractional volume of blood per MRI visible matter (Vb).

11. The method according to claim 8 further comprising calculating with the compartmental model algorithm diffusing capacity of the vasculature ($K_{ox}$).

12. The method according to claim 8 further comprising calculating with the compartmental model algorithm $M_{ox}$, the metabolic consumption rate.

13. The method according to claim 8 wherein the compartmental model algorithm incorporates a term indicative of the concentration of oxygen in the blood ($C_b$).

14. The method of claim 13 further comprising calculating the concentration of oxygen in the blood ($C_b$) from the concentration of breathed oxygen ($PIO_2$).

15. The method according to claim 13 further comprising calculating $C_b$ with regard to an estimated wash-in or wash-out time for the blood ($T_{OIF}$).

16. The method according to claim 13 wherein $C_b$ is determined from a measurement of oxygen concentration in the blood.

17. The method according to claim 16 wherein the measurement of oxygen concentration in the blood is measured from OE-MRI data.

18. The method of claim 17 wherein the OE-MRI data is taken from a region of the subject which includes the aorta.

19. A method of characterising function of tissues of a body that receive oxygen from a vascular supply in a subject in need of such characterization, the method comprising:
performing, with an imaging system having a computer and a processor, an Oxygen-Enhanced Magnetic Resonance Imaging (OE-MRI) on a tissue space associated with the tissue of interest,
generating image data, with the imaging system, over a time period during which the subject inhales gases with at least two different partial pressures of oxygen, the image data providing information in respect of delivery of oxygen to a tissue and metabolic consumption of oxygen within the tissue; and
applying, with the processor, a compartmental model algorithm to the image data generated to provide information on metabolic rate of oxygen consumption of the tissue, wherein the compartmental model algorithm is a two-compartment model based on physiological parameters for rate of delivery, diffusion and metabolisation, wherein the algorithm is:

$$C_T = (1 - V_e)C_b + K_{ox} \int C_b(\tau) \exp\left(-\frac{K_{ox} + M_{ox}}{V_e}(t - \tau)\right) d\tau$$

where:
$K_{ox}$ is the diffusing capacity of the vasculature;
$M_{ox}$ is the metabolic consumption rate;
$C_b$ is a term indicative of the concentration of oxygen in the blood; and
$V_e$ is the fractional volume of tissue or interstitium per MRI visible matter.

20. An apparatus for generating and characterizing data concerning function of tissues of a body that receive oxygen from a vascular supply in a subject, the apparatus comprising:
a computer in communication with the apparatus;
a memory storing processor readable instructions; and
a processor configured to read and execute instructions stored in said memory, the processor being operable to perform an Oxygen-Enhanced Magnetic Resonance Imaging (OE-MRI) on a tissue space associated with the tissue of interest,
generate image data over a time period during which the subject inhales gases with at least two different partial pressures of oxygen, the image data providing information in respect of delivery of oxygen to a tissue and metabolic consumption of oxygen within the tissue, and
apply a compartmental model algorithm, that includes a metabolic factor, to the image data generated to provide information on metabolic rate of oxygen consumption of the tissue,
wherein the compartmental model algorithm includes a factor associated with metabolic consumption of oxygen in the tissue.

21. A non-transitory computer readable medium comprising computer readable program code for characterizing data concerning function of tissues of a body that receive oxygen from a vascular supply in a subject, the program code configured to cause a computer to perform an Oxygen-Enhanced Magnetic Resonance Imaging (OE-MRI) on a tissue space associated with the tissue of interest,
generate image data over a time period during which the subject inhales gases with at least two different partial pressures of oxygen, the image data providing information in respect of delivery of oxygen to a tissue and metabolic consumption of oxygen within the tissue, and
apply a compartmental model algorithm, that includes a factor associated with metabolic consumption of oxygen in the tissue, to the image data generated to provide information on metabolic rate of oxygen consumption of the tissue.

* * * * *